(12) United States Patent
Gourse et al.

(10) Patent No.: US 6,605,431 B1
(45) Date of Patent: Aug. 12, 2003

(54) PROMOTER ELEMENTS AND METHODS OF USE

(75) Inventors: Richard L. Gourse, Madison, WI (US); Shawn T. Estrem, Greenwood, IN (US); Wilma E. Ross, Madison, WI (US); Tamas Gaal, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 09/375,673

(22) Filed: Aug. 17, 1999

(51) Int. Cl.[7] .......................... C12Q 1/68; C12P 19/34; C12N 9/38; C07H 21/04
(52) U.S. Cl. ........................ 435/6; 435/91.2; 435/207; 536/23.1
(58) Field of Search .......................... 435/6, 207, 91.2; 536/23.1

(56) References Cited

U.S. PATENT DOCUMENTS 6,111,077 A * 8/2000 Sonenberg et al. ......... 530/350

OTHER PUBLICATIONS

Abstract of NIH Grant No. RO1GM37048–01–03 for project entitled "Mechanism, Activation, and Control of rRNA Transcription," (1985).
Abstract of NIH Grant No. RO1GM37048–04–08 for project entitled "Mechanism, Activation, and Control of rRNA Transcription,"(1990–1994).
Abstract of NIH Grant No. RO1GM37048–09–12 for project entitled "Mechanism, Activation, and Control of rRNA Transcription,"(1995–1998).
S. E. Aiyar et al., "Upstream A–tracts Increase Bacterial Promoter Activity Through Interactions with the RNA Polymerase Subunit," *Proc. Natl. Acad. Sci. USA*, 95: 14652–14657 (1998).
Title page, copyright page, and table of contents for F. M. Ausubel et al., Ed. *Current Protocols in Molecular Biology*, vol. 2, John Wiley & Sons, NY (1989).
T. K. Blackwell et al., "Differences and Similarities in DNA–Binding Preferences of MyoD and E2A Protein Complexes Revealed by Binding Site Selection," *Science*, 250: 1104–1110 (1990).
E. E. Blatter et al., "Domain Organization of RNA Polymerase Subunit: C–Terminal 85 Amino Acids Constitute a Domain Capable of Dimerization and DNA Binding," *Cell*, 78: 889–896 (1994).
L. Bracco et al., "Synthetic Curved DNA Sequences Can Act as Transcriptional Activators in *Escherichia coli*," *EMBO J.*, 9: 4289–4296 (1989).
R. R. Burgess et al., "A Procedure for the Rapid, Large–Scale Purification of *Escherichia coli* DNA–Dependent RNA Polymerase Involving Polymin P Precipitation and DNA–Dellulose Chromatography," *Biochem.*, 14: 4634–4638 (1975).

M. Coll et al., "A Bifurcated Hydrogen–Bonded Conformation in the d(A●T) Base Pairs of the DNA Dodecamer d(CGCAAATTTGCG) and Its Complex with Distamycin," *Proc. Natl. Acad. Sci. USA*, 84: 8385–8389 (1987).
T. Ellinger et al., "Context–Dependent Effects of Upstream A–Tracts: Stimulation of Inhibition of *Escherichia coli* Promoter Function," *J. Mol. Biol.*, 239: 466–475 (1994).
Abstract and poster of S. T. Estrem et al. entitled "Determination of the UP Element Consensus Sequence," presented at the Molecular Genetics of Bacteria and Phages Meeting (Aug. 5–Aug. 10, 1997) in Madison, Wisconsin.
S. T. Estrem et al., "Identification of an UDP Element Consensus Sequence for Bacterial Promoters," *Proc. Natl. Acad. Sci. USA*, 95: 9761–9766 (1998).
S. T. Estrem et al., "Bacterial Promoter Architecture: Subsite Structure of UP Elements and Interactions with the Carboxy–Terminal Domain of the RNA Polymerase Subunit," *Genes & Dev.*, 13(16): 2134–2147 (1999).
K. Frederick et al., "Promoter Architecture in the Flagellar Regulon of *Bacillus subtilis*: High–Level Expression of Flagellin by the $\sigma^D$ RNA Polymerase Requires an Upstream Promoter Element," *Proc. Natl. Acad. Sci. USA*, 92: 2582–2586 (1995).
T. Gaal et al., "Saturation Mutagenesis of an *Escherichia coli* rRNA Promoter and Initial Characterization of Promoter Variants," *J. Bacteriol.*, 171: 4852–4861 (1989).
T. Gaal et al., "DNA–Binding Determinants of the Subunit of RNA Polymerase: Novel DNA–Binding Domain Architecture," *Genes and Development*, 10: 16–26 (1996).
H. Giladi et al., "Identification of an UP Element Within IHF Binding Site at the $P_L1-P_L2$ Tandem Promoter of Bacteriophage λ," *J. Mol. Biol.*, 260: 484–491 (1996).
R. L. Gourse et al., "DNA Determinants of rRNA Synthesis in *E. coli*: Growth Rate Dependent Regulation, Feedback Inhibition, Upstream Activation, Antitermination," *Cell*, 44: 197–205 (1986).
R. L. Gourse et al., "Strength and Regulation without Transcription Factors: Lessons from Bacterial rRNA Promoters," *Cold Spring Harbor Symp Quant Biol., vol. LXIII,* Cold Spring Harbor Laboratory Press, Cold Spring Harbor, NY pp. 131–139 (1998).

(List continued on next page.)

Primary Examiner—Gary Benzion
Assistant Examiner—Joyce Tung
(74) Attorney, Agent, or Firm—Mueting, Raasch & Gebhardt, P.A.

(57) ABSTRACT

The present invention provides novel polynucleotides that include promoter elements. The present invention also provides methods and kits for identification of compounds that alter transcription, preferably decrease transcription, of a polynucleotide. Also provided by the present invention are methods directed to producing RNA polynucleotides and polypeptides.

12 Claims, 6 Drawing Sheets

OTHER PUBLICATIONS

M. C.. Graves et al., "In Vivo and In Vitro Transcription of the *Clostridium pasteurianum* Ferredoxin Gene: Evidence for "Extended" Promoter Elements in Gram–Positive Organisms," *J. Biol. Chem.*, 261: 11409–11415 (1986).

D. K. Hawley et al., "Compilation and Analysis of *Escherichia coli* Promoter DNA Sequences," *Nucl. Acids Res.*, 11: 2237–2255 (1983).

J. D. Helmann, "Compilation and Analysis of *Bacillus subtilis* $\sigma^A$–Dependent Promoter Sequences: Evidence for Extended Contact Between RNA Polymerase and Upstream Promoter DNA," *Nucl. Acids Res.*, 23: 2351–2360 (1995).

C. A. Josaitis et al., "Sequences Upstream of the −35 Hexamer of rrnB P1 Affect Promoter Strength and Upstream Activation," *Biochem. Biophys. Acta*, 1050: 307–311 (1990).

S. Lisser et al., "Compilation of *E. coli* mRNA Promoter Sequences," *Nucl. Acids Res.*, 21: 1507–1516 (1993).

C. F. McAllister et al., "Rotational Orientation of Upstream Curved DNA Affects Promoter Function in *Bacillus subtilis*," *J. Biol. Chem.*, 264: 10451–10456 (1989).

J. H. Miller et al., "Experiment 48: Assay of β–Galactosidase," in *Experiments in Molecular Genetics*, Cold Spring Harbor Laboratory, Cold Spring Harbor Laboratory, NY pp. 352–355 (1972).

A. Miura et al., "Growth–Rate–Dependent Regulation of Ribosome Synthesis in *E. coli*: Expression of the lacZ and galK Genes Fused to Ribosomal Promoters," *Cell*, 25: 773–782 (1981).

K. Murakami et al., "Transcriptional Factor Recognition Surface on the RNA Polymerase Subunit is Involved in Contact with the DNA Enhancer Element," *EMBO J.*, 15: 4358–4367 (1996).

J. T. Newlands et al., "Both Fis–Dependent and Factor–Independent Upstream Activation of the rrnB P1 Promoter are Face of the Helix Dependent," *Nucl. Acids Res.*, 20: 719–726 (1992).

J. T. Newlands et al., "Factor–Independent Activation of *Escherichia coli* rRNA Transcription," *J. Mol. Biol.*, 220: 569–583 (1991).

J. T. Newlands et al., "Transcription of the *Escherichia coli* rrnB P1 Promoter by the Heat Shock RNA Polymerase (E$\sigma^{32}$) In Vitro," *J. Bacteriol.*, 175: 661–668 (1993).

R. Pollock et al. "A Sensitive Method for the Determination of Protein–DNA Binding Specificities," *Nucl. Acids Res.*, 18: 6197–6204 (1990).

B. S. Powell et al., "Rapid Confirmation of Single Copy Lambda Prophage Integration by PCR," *Nucl. Acids Res.*, 22: 5765–5766 (1994).

L. Rao et al., "Factor Independent Activation of rrnB P1: An "Extended" Promoter with an Upstream Element that Dramatically Increases Promoter Strength," *J. Mol. Biol.*, 235: 1421–1435 (1994).

W. Ross et al., "*Escherichia Coli* Promoters with UDP Elements of Different Strengths: Modular Structure of Bacterial Promoters," *J. of Bacteriology*, 180: 5375–5383 (1998).

W. Ross et al., "A Third Recognition Element in Bacterial Promoters: DNA Binding by the Subunit of RNA Polymerase," *Science*, 262: 1407–1413 (1993).

W. Ross et al., "*E.coli* Fis Protein Activates Ribosomal RNA Transcription In Vitro and In Vivo," *EMBO J.*, 9: 3733–3742 (1990).

Title page, copyright page, and table of contents for Sambrook et al, *Molecular Cloning: A Laboratory Manual.*, Cold Spring Harbor Laboratory Press (1989).

H. Tang et al., "*Escherichia coli* RNA Polymerase Holoenzyme: Rapid Reconstitution from Recombinant , β, β', and σ Subunits," *Meth. Enzymol.*, 273: 130–134 (1996).

Y. Tang et al., "Upstream Interactions at the Lambda $P_{RM}$ Promoter Are Sequence Nonspecific and Activate the Promoter to a Lesser Extent than an Introduced UP Element of an rRNA Promoter," *J. Bacteriol.*, 178: 6945–6951 (1996).

C. Tuerk et al., "Systematic Evolution of Ligands by Exponential Enrichment: RNA Ligands to Bacteriophage T4 DNA Polymerase," *Science*, 249: 505–510 (1990).

W. E. Wright et al., "Cyclic Amplification and Selection of Targets (CASTing) for the Myogenin Consensus Binding Site," *Mol. Cell Biol.*, 11: 4104–4110 (1991).

P. van Ulsen et al., "Function of the C–Terminal Domain of the Alpha Subunit of *Escherichia coli* RNA Polymerase in Basal Expression and Integration Host Factor–Mediated Activation of the Early Promoter of Bacteriophage Mu," *J. Bacteriol.*, 179: 530–537 (1997).

H. Yang et al., "Differential Sensitivity of Gene Expression in vitro to Inhibitors of DNA Gyrase," *Proc. Natl. Acad. Sci. USA*, 76: 3304–3308 (1979).

\* cited by examiner

| | Upstream Sequence Name | Relative Activity | Upstream Sequence | rrnB P1 Core Promoter |
|---|---|---|---|---|
| | | | -59          -50          -38 | |
| SEQ. ID NO: | | | | -35   -10 |
| 40 | 4192 | 326 | ggaaaattttttttcaaaagta | |
| 41 | 4181 | 320 | agaaattttttttcgaaaaaca | |
| 42 | 4176 | 316 | taaaaattttttttgaaaaggg | |
| 43 | 4173 | 297 | caaaaatattttttgaaaaaaga | |
| 44 | 4209* | 293 | ggaaatattttttcataaaccc | |
| 45 | 4206 | 274 | agaaaaatattttcgaaaacta | |
| 46 | 4202 | 269 | aaaaatattttttcgaaaagta | |
| 47 | 4196 | 268 | taaattttttttttgcaaaagta | |
| 48 | 4193 | 265 | acaaaaatattttttcaaaaccc | |
| 49 | 4179 | 265 | ttaaattttttttcgtaaaccc | |
| 50 | 4203 | 262 | ttaaattttttttcataaaccc | |
| 51 | 4191 | 262 | tcaaattttttttgcaaaccc | |
| 52 | 4204 | 257 | caaattttttttgctaaaccc | |
| 53 | 4190 | 248 | aaaaatattttttttgaaaagta | |
| 54 | 4219* | 245 | taaaaatattttcgtttaccc | |
| 55 | 4198 | 240 | acaaaaatattttcgaaaccc | |
| 56 | 4200 | 239 | tcaaaattttttttgcaaagta | |
| 57 | 4218* | 238 | tgaattttttttcgtctaccc | |
| 58 | 4171 | 228 | agaaaaatattttgaaaacta | |
| 59 | 4177 | 222 | gcaaaataattgtaaaaagta | |
| 60 | 4220* | 221 | agaaatttatttttaaaaaggg | |
| 61 | 4205 | 215 | tgaaaaatattttttgaaaacta | |
| 62 | 4199 | 213 | taaactatttttttcaaaaagga | |
| 63 | 4174 | 210 | tgaaatttattttgcgaaaggg | |
| 64 | 4197 | 206 | taaactttttttttcgaaagtg | |
| 65 | 4207 | 199 | tgaaatattttttttgaaaaccc | |
| 66 | 4194 | 194 | agattttttttttgtaaaagtg | |
| 67 | 4168 | 193 | gcaaaaatatttcgtcaaaccc | |
| 68 | 4201 | 185 | gaaaaatattttttgataaagta | |
| 69 | 4185 | 178 | gcaaaattattttgctaaagta | |
| 70 | 4195 | 136 | gaaatatattttttcaaaagta | |
| 71 | WT-rrnB P1 | 69 | agaaaattattttaaatttcct | |
| 72 | core rrnB P1 | 1 | gactgcagtggtacctaggaat | |

Fig. 2A

|   | -55 | | | | | | | | -50 | | | | | | -45 | | | | | -40 | |
|---|---|---|---|---|---|---|---|---|---|---|---|---|---|---|---|---|---|---|---|---|---|
| A | 29 | 35 | 100 | 97 | 81 | 45 | 39 | 13 | 35 | 0 | 0 | 0 | 0 | 6 | 23 | 55 | 94 | 94 | 100 | 6 | 0 | 48 |
| T | 42 | 6 | 0 | 3 | 13 | 55 | 61 | 87 | 65 | 100 | 100 | 97 | 97 | 39 | 6 | 26 | 3 | 6 | 0 | 0 | 45 | 0 |
| G | 23 | 35 | 0 | 0 | 0 | 0 | 0 | 0 | 0 | 0 | 0 | 3 | 0 | 26 | 42 | 10 | 0 | 0 | 0 | 48 | 16 | 16 |
| C | 6 | 23 | 0 | 0 | 6 | 0 | 0 | 0 | 0 | 0 | 0 | 0 | 3 | 29 | 29 | 10 | 3 | 0 | 0 | 45 | 39 | 35 |

-59                      -31    SEQ. ID NO:
     GACTGCAGTGGTANNNNNNNNNCTTGTCA    39
```

| Name and No. of isolates | | Relative Activity | Proximal subsite Sequence | |
|---|---|---|---|---|
| 4549 | (3) | 170 | aaaaaaaga | 29 |
| 4546 | (3) | 160 | aaaaaaaca | 30 |
| 4544 | (3) | 160 | aaaaaaatg | 31 |
| 4547 | (2) | 130 | aaaaaagta | 32 |
| 4548 | (5) | 130 | aaaaaagtg | 33 |
| 4542* | (1) | 130 | aaaatagta | 34 |
| 4545 | (1) | 110 | caaaaaaca | 35 |
| 4543* | (1) | 82 | aaaaaaata | 36 |
| rrnB P1 Proximal | | 20 | aaatttcct | 37 |
| No UP | | 1 | cctaggaat | 38 |

|   | -46 |    | -44 |    | -42 |    | -40 |    | -38 |
|---|---|---|---|---|---|---|---|---|---|
| A | 88 | 100 | 100 | 100 | 88 | 100 | 63 | 0 | 75 |
| T | 0 | 0 | 0 | 0 | 12 | 0 | 0 | 63 | 0 |
| G | 0 | 0 | 0 | 0 | 0 | 0 | 37 | 12 | 25 |
| C | 12 | 0 | 0 | 0 | 0 | 0 | 0 | 25 | 0 |

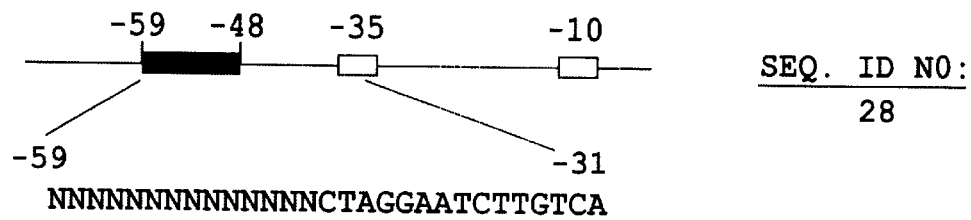

```
         -59  -48      -35           -10
    ─────███████████───▢▢▢▢──────────▢▢▢▢─────         SEQ. ID NO:
                                                              28
   -59                                    -31
       NNNNNNNNNNNNNNNNNNCTAGGAATCTTGTCA
```

Fig. 4A

| Name and No. of isolates | | Relative Activity | Distal subsite Sequence | |
|---|---|---|---|---|
| 4518 | (2) | 16 | agaaaaatattttg | 6 |
| 4517 | (1) | 15 | gcattttttttca | 7 |
| 4512* | (1) | 14 | gtaaaaatttttta | 8 |
| 4520 | (1) | 13 | acgtatttttttta | 9 |
| 4521 | (1) | 12 | gaaaaatattttg | 10 |
| 4511 | (2) | 12 | taaaaaatatttta | 11 |
| 4515 | (1) | 12 | taagttttttttta | 12 |
| 4503 | (1) | 11 | aaaatttattttg | 13 |
| 4507* | (1) | 10 | cgaaaaaaaattta | 14 |
| 4509 | (1) | 10 | ccggtttttttta | 15 |
| 4500 | (1) | 9 | taaatttttttttt | 16 |
| 4516 | (1) | 9 | gaaaaaaatagttg | 17 |
| 4514 | (1) | 7 | atatgtttttttta | 18 |
| 4505 | (1) | 6 | agatttatttttct | 19 |
| 4504 | (1) | 5 | gataaaaatagttg | 20 |
| 4510 | (1) | 5 | gtatgattttttta | 21 |
| 4508 | (1) | 5 | ataaaatattttat | 22 |
| 4519 | (1) | 4 | gcaaatatattttt | 23 |
| 4501 | (1) | 4 | tgtaataatttta | 24 |
| rrnB P1 Distal | | 9 | agaaaattattta | 25 |
| No Up | | 1 | gactgcagtggtac | 26 |
| 4513 | | 16 | ggaaaattttttttt | 27 |

| Consensus Sequences | | SEQ. ID NO: |
|---|---|---|
| Combined Proximal subsite | NNAAAWWTWTTTTNNNAAANNN | 2 |
| | AAAAAARNR | 3 |
| Distal Subsite | NNAWWWWWTTTTN | 4 |

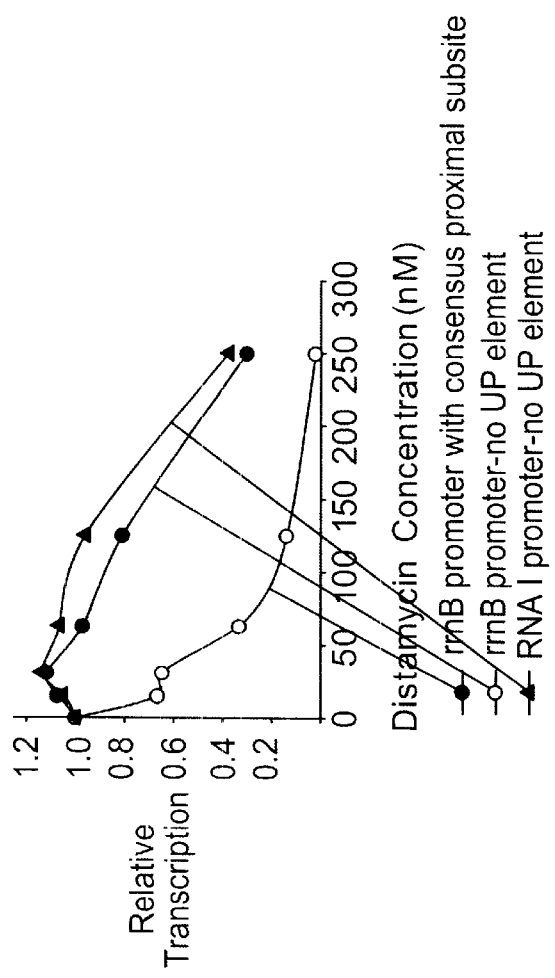
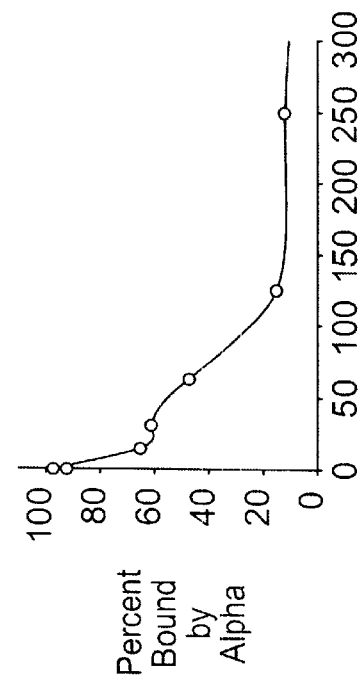
Fig. 6A
Fig. 6B
Distamycin Inhibits Alpha Binding to DNA and UP Element-dependent Stimulation of Transcription

PROMOTER ELEMENTS AND METHODS OF USE

GOVERNMENT FUNDING

The present invention was made with government support under Grant No. RO1GM37048, awarded by the National Institutes of Health. The Government may have certain rights in this invention.

BACKGROUND

The expression of genes in prokaryotes is a complex process that involves several steps. One of the first steps is transcription of the gene by an RNA polymerase (RNAP). Transcription is initiated after an RNA polymerase recognizes and binds to a region of nucleotides upstream of the nucleotides that are transcribed. This region is typically referred to as a promoter. Transcription factor binding sites are often located near promoters. In contrast to promoters, transcription factor binding sites are nucleotide sequences to which transcription factors bind. A bound transcription factor then interacts with the RNA polymerase to increase the affinity of the RNA polymerase for the promoter, or to increase the rates of later steps in the mechanism of transcription.

*Escherichia coli* promoters recognized by the major form of RNA polymerase (RNAP E$\sigma^{70}$) typically contain at least two nucleotide sequences that the RNA polymerase recognizes. The first is a hexamer centered approximately 10 base pairs upstream of the transcription start site, and is referred to as the −10 sequence. The second is also a hexamer, and is referred to as the −35 sequence. Typically, about 16 to about 18 base pairs separate the −35 sequence and the −10 sequence in a promoter; however, as few as about 15 base pairs and as many as about 20 base pairs have been observed to separate the −35 sequence and the −10 sequence. The −35 sequence and the −10 sequence are recognized by the a subunit of RNAP.

A third recognition element, referred to in the art as the UP element, has been identified upstream of the −35 sequence (Ross, W. et al. (1993) *Science* 262, 1407–1413). The most extensively characterized UP element is an adenosine and thymidine rich sequence located between about nucleotide −40 and about nucleotide −60 in the rrnB P1 promoter (i.e., about 40 to about 60 nucleotides 5' or upstream of the transcription initiation site). The UP element is believed to stimulate promoter activity by increasing the initial equilibrium constant ($K_B$) and possibly later step(s) in the transcription initiation pathway ($k_f$) (Ross, W. et al. (1993) *Science* 262, 1407–1413; Rao, L. et al. (1994) *J. Mol. Biol.* 235, 1421–1435).

RNAP E$\sigma^{70}$ is composed of 2 α subunits, a β subunit, a β' subunit, and a σ subunit. Each RNAP α subunit consists of two domains, a 28 kDa N-terminal domain and an 8 kDa C-terminal domain (αCTD) connected by a long unstructured and/or flexible linker (Blatter, E. E. et al. (1994) *Cell* 78, 889–896). The UP element is recognized by the αCTD of RNAP. The seven αCTD residues most crucial for DNA binding (L262, R265, N268, C269, G296, K298, S299) are highly conserved in bacteria (Gaal, T. et al. (1996) *Genes Develop.* 10, 16–26). Despite the importance of the αCTD-DNA interaction for bacterial transcription, the details of DNA recognition by a remain to be elucidated.

UP elements have also been described in other promoters and can function with holoenzymes containing different a factors (Ross, W. et al. (1993) *Science* 262, 1407–1413; Newlands, J. T. et al. (1993) *J. Bacteriol.* 175, 661–668; Fredrick, K. et al. (1995) *Proc. Natl. Acad. Sci. USA* 92, 2582–2586; Giladi, H. et al. (1996) *J. Mol. Biol.* 260, 484–491; van Ulsen, P. et al. (1997) *J. Bacteriol.* 179, 530–537). It appears that UP element-like sequences occur frequently in promoters from gram positive bacteria (Helman, J. D. (1995) *Nucl. Acids Res.* 23, 2351–2360; Graves, M. C. et al. (1986) *J. Biol. Chem.* 261, 11409–11415). Consensus sequences derived previously from *E. coli* promoters contain highly conserved −10 and −35 hexamers; however, no highly conserved upstream sequences have been identified.

SUMMARY OF THE INVENTION

In the recent past there has been a significant increase in the prevalence of antibiotic resistant bacteria. However, the identification of new anti-bacterial compounds has not kept pace with the occurrence of these bacteria. Accordingly, there has been a significant increase in human and animal morbidity and mortality due to infectious diseases. The present invention represents a significant advance in the art of identifying compounds that inhibit the transcription of certain promoters, preferably bacterial promoters. Such compounds can be used to inhibit the expression of transcription units and are expected to inhibit the growth of bacteria Prior to the present invention, there were not enough accessory promoter elements (of the type known to the art as UP elements) characterized to derive a consensus sequence accessory promoter element. Therefore, an in vitro selection was developed and followed by an in vivo screen to identify accessory promoter elements from a random DNA population that greatly increased promoter activity. Accessory promoter elements were identified that conferred larger increases on rrnB P1 core promoter activity than any previously identified accessory promoter elements, and a consensus accessory promoter element was derived. The same type of in vitro selection and in vivo screen was also used to identify two portions of the consensus accessory promoter element. These two portions, referred to herein as the distal subsite and the proximal subsite, each conferred increases on rrnB P1 core promoter activity. An advantage of a preferred aspect of the present invention is the increased sensitivity to compounds that inhibit transcription: the higher levels of transcription by promoters of the invention allow changes in transcription to be more easily measured.

Accordingly, the present invention provides a method for detecting whether a compound alters transcription of a transcription unit. The method includes providing in a reaction mixture a first polynucleotide that includes a promoter operably linked to a transcription unit, adding an amount of the compound to be tested to the reaction mixture under conditions effective to cause transcription, detecting an amount of a transcription product, and comparing the amount of the transcription product in the presence of the compound to an amount of the transcription product in the absence of the compound under the same conditions. The promoter includes an accessory promoter element and a core promoter element, and the reaction mixture includes at least one RNA polymerase. Optionally, the compound does not alter the amount of a transcription product from a second polynucleotide, where the second polynucleotide includes a second promoter operably linked to the same transcription unit that is operably linked to the first promoter, where the second promoter includes the same core promoter element of the first promoter and not an accessory promoter element. Typically, transcription of the transcription unit is decreased; The polynucleotide can be present on a plasmid vector.

Optionally, the reaction mixture can include an rNTP that includes a detectable label. The detectable label can be a radioactive label, a fluorescent label, or an enzymatic label, or a combination. Optionally, the transcription unit can also include a coding region that optionally encodes a detectable marker. The detectable marker can be β-galactosidase, green fluorescent protein, luciferase, or chloramphenicol acetyl transferase. The reaction mixture can include a detectably labeled amino acid. The detectable label can be a radioactive label, a fluorescent label, an enzymatic label, and a combination thereof.

The accessory promoter element can be a distal accessory promoter element, a proximal accessory promoter element, or a combined accessory promoter element. The distal accessory promoter element can include the nucleotide sequence of SEQ ID NOs:4, 6–24, 27, or complements thereof. When a series of sequence identification numbers are disclosed herein, it should be understood that each sequence can be used separately. For instance, stating that an accessory promoter element can include the nucleotide sequence of SEQ ID NOs:4, 6–24, or 27 means the nucleotide sequence can be SEQ ID NO:4, or SEQ ID NO:6, or SEQ ID NO:7, etc. The proximal accessory promoter element can include the nucleotide sequence of SEQ ID NOs:3, 29–36, or complements thereof. The combined accessory promoter element can include a nucleotide sequence of SEQ ID NOs:1–2, 40–70, or complements thereof.

The present invention also provides a kit for testing the ability of a compound to alter transcription of a transcription unit. The kit includes a first polynucleotide that includes a first promoter operably linked to a transcription unit. The first promoter includes an accessory promoter element and a core promoter element. Optionally, the kit includes a second polynucleotide that includes a second promoter operably linked to the same transcription unit that is operably linked to the first promoter. The second promoter includes the same core promoter element of the first promoter and not an accessory promoter element. The polynucleotide can be present on a plasmid vector.

Optionally, the kit can include at least one rNTP that includes a detectable label. The detectable label can be a radioactive label, a fluorescent label, an enzymatic label, or a combination thereof Optionally, the transcription unit can also include a coding region that optionally encodes a detectable marker. The detectable marker can be β-galactosidase, green fluorescent protein, luciferase, or chloramphenicol acetyl transferase. The kit can include a detectably labeled amino acid. The detectable label can be a radioactive label, a fluorescent label, an enzymatic label, and a combination thereof.

For the kits of the present invention, the accessory promoter element can be a distal accessory promoter element, a proximal accessory promoter element, or combined accessory promoter element. The distal accessory promoter element can include the nucleotide sequence of SEQ ID NOs:4, 6–24, 27, or complements thereof. The proximal accessory promoter element can include the nucleotide sequence of SEQ ID NOs:3, 29–36, or complements thereof. The combined accessory promoter element can include a nucleotide sequence of SEQ ID NOs: 1–2, 40–70, or complements thereof.

Promoters are used in recombinant DNA techniques to express RNA polynucleotides or polypeptides in bacterial strains. The RNA polynucleotides or polypeptides can be naturally present in a bacterial strain, or can be from a different type of cell, for instance a different bacterial cell or an animal cell. Isolated RNA polynucleotides or polypeptides are useful in, for example, the development of antibodies, vaccines, and drugs to modify the activity of an RNA polynucleotide or polypeptide, but the ability to isolate RNA polynucleotides or polypeptides is often hampered by low levels of expression in a bacterial strain. Thus, there is a continuing need for the development of methods to increase expression of RNA polynucleotides and/or polypeptides by bacterial cells. The present invention also represents an advance in the art of producing RNA polynucleotides and/or polypeptides by providing promoters that increase transcription and the resulting synthesis of RNA polynucleotides and/or polypeptides.

Prior to the present invention, transcription factor binding sites were often used to increase transcription of a promoter. The use of transcription factors to increase transcription requires not only the use of bacterial cells that encode the correct transcription factors, but growth of the cells under conditions such that the transcription factors are expressed. The promoters of the present invention obviate the need for transcription factor binding sites and transcription factors to increase transcription. Accordingly, the present invention also provides a method of producing an RNA polynucleotide. The method includes introducing to a bacterium a polynucleotide that includes a promoter operably linked to a transcription unit, incubating the bacterium under conditions that promote expression of the transcription unit such that an RNA polynucleotide encoded by the transcription unit is produced, and isolating the RNA polynucleotide. The promoter includes an accessory promoter element and a core promoter element. The RNA polynucleotide can be a structural RNA, an antisense RNA, or a catalytic RNA.

The present invention further provides a method of producing a polypeptide. The method includes introducing to a bacterium a polynucleotide that includes a promoter operably linked to a transcription unit including a coding region, incubating the bacterium under conditions that promote expression of the coding region such that a polypeptide encoded by the coding region is produced, and isolating the polypeptide. The promoter includes an accessory promoter element and a core promoter element. The polynucleotide can be present on a plasmid vector.

For the methods of the present invention, the accessory promoter element can be a distal accessory promoter element, a proximal accessory promoter element, or a combined accessory promoter element. The distal accessory promoter element can include the nucleotide sequence of SEQ ID NOs:4, 6–24, 27, or complements thereof. The proximal accessory promoter element can include the nucleotide sequence of SEQ ID NOs:3, 29–36, or complements thereof. The combined accessory promoter element can include a nucleotide sequence of SEQ ID NOs: 1–2, 40–70, or complements thereof.

The present invention further provides kits for expressing an RNA polynucleotide or a polypeptide. The kits include a polynucleotide that includes a promoter and at least one restriction endonuclease site. The promoter includes an accessory promoter element and a core promoter element, and the restriction endonuclease site is present 3' of the promoter and provides an insertion site for a transcription unit encoding an RNA polynucleotide, or a coding region encoding a polypeptide.

Also provided by the present invention are polynucleotides. The polynucleotides include an accessory promoter element having a nucleotide sequence of SEQ ID NOs: 1–4, 6–24, 27, 29–36, 40–70, or complements thereof.

BRIEF DESCRIPTION OF THE FIGURES

FIG. 2. Upstream sequences and relative transcription activities of 31 in vitro-selected promoters used in defining a combined UP element consensus sequence. A. Promoters contained wild type rrnB P1 sequences (solid line; open boxes indicate the −10 and −35 hexamers) and different upstream regions (dotted line). Sequences of the non-template strand in the upstream region (−59 to −38) from 31 selected promoters, wild type rrnB P1, and the rrnB P1 core promoter (which lacks an UP element) are shown. Upstream sequence names are the strain numbers of λ lysogens carrying the promoter-lacZ fusions Asterisks indicate promoters with single base pair mutations (probably introduced during PCR amplification) downstream of the transcription start site (between +2 and +17). Sequence variation in this region of rrnB P1 does not affect promoter activity. Promoter activities are expressed relative to the activity of the core rrnB P1 promoter (activity=1; strain RLG3Q97) and were determined from β-galactosidase measurements in λ lysogens containing promoter-lacZ fusions. Relative activities differed by less than 10% in at least two different experiments. B. Nucleotide frequencies (percentage of 31 sequences) at each position, −59 to −38, in the set of selected sequences shown in A.

FIG. 4. Distal subsites. Sequences and relative activities of 19 promoters selected for binding of RNAP in vitro and screened for high transcription in vivo. A. Details are described in FIG. 3, except the promoters contained the sequence in the proximal region (−45 to −38 CTAGGAAT), and different distal regions (filled rectangle; −59 to −46). The randomized residues are indicated as "N" and displayed in context (non-template strand) below the schematic in B. The −35 hexamer is in boldface. B. Distal subsite sequences (i.e., distal accessory promoter elements) are shown for 19 selected promoters, for an rrnB P1 construct containing only the distal region of the rrnB P1 UP element ("rrnB P1 Distal"; RLG3099), and for a construct lacking an UP element ("No UP"; RLG3097). Distal subsite 4513 is described in the text. C. Nucleotide frequencies (percentage of 19 sequences shown in FIG. 4B) for each proximal subsite position (−59 to −46).

FIG. 6. Distamycin inhibits the binding of α subunit to DNA. A. Gel shift assay of distamycin concentration versus percent of DNA fragments containing the proximal accessory promoter element 4547 bound by distamycin. B. In vitro transcription of promoters containing or lacking a proximal accessory element. rrnB promoter with consensus proximal subsite, contains the proximal accessory promoter element 4547; rrnB promoter—no UP element, contains the element shown at SEQ ID NO:38.

DETAILED DESCRIPTION OF PREFERRED EMBODIMENTS OF THE INVENTION

Figure 1A:
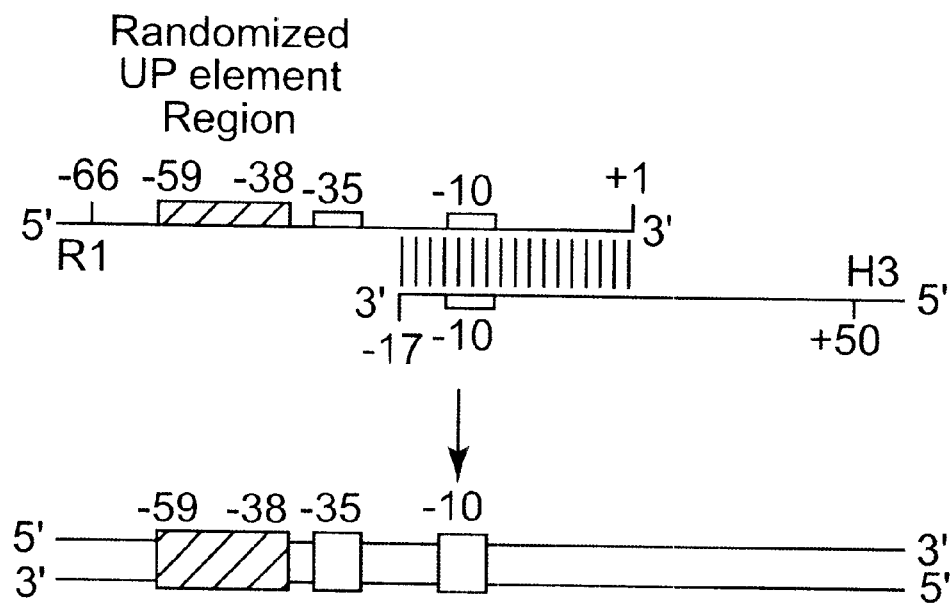
FIG. 1. In vitro selection. A. Synthesis of rrnB P1 promoter fragments with a randomized upstream region. The randomized region is labeled and indicated by a hatched box; the −10 and −35 of rrnB P1 are indicated by open boxes; the numbers −66 and +1 on the top strand and the −17 and +50 on the bottom strand refer to the location of nucleotides relative to the distance from the first transcribed nucleotide, i.e., nucleotide +1; the vertical lines between the top and bottom strands signify the base pairing of the nucleotides on the top strand with the complementary nucleotides on the bottom strand; RI refers to EcoRI and H3 refers to HinDIII. B. Theoretical time course of RNAP binding to promoters containing (UP$^+$) or lacking (UP$^-$) an UP element. The dashed line represents a time at which RNAP-promoter binding reactions were stopped in order to enrich for UP element-containing fragments.

The present invention provides novel polynucleotides and methods of using the polynucleotides. In one aspect of the invention, methods are directed to the identification of compounds that alter transcription, preferably decrease transcription, of a polynucleotide. "Polynucleotide" as used herein refers to a polymeric form of nucleotides of any length, either ribonucleotides (rNTPs) or deoxyribonucleotides (dNTPs), and includes both double- and single-stranded DNA and RNA. Examples of polynucleotides include, for example, promoters, transcription units, coding regions, and regulatory regions, which are described herein. A polynucleotide can be obtained directly from a natural source (e.g., a bacterium), or can be prepared with the aid of recombinant, enzymatic, or chemical techniques. A polynucleotide can be linear or circular in topology. A polynucleotide can be, for example, a portion of a vector, such as an expression or cloning vector. Preferably, a polynucleotide is isolated. As used herein, the term "isolated" means that a polynucleotide (or a polypeptide) is either removed from its natural environment or synthetically derived. Preferably, the polynucleotide (or polypeptide) is purified, i.e., essentially free from any other polynucleotides (or polypeptides) and associated cellular products or other impurities.

Methods of the present invention directed to the identification of compounds that alter transcription of a polynucleotide include adding an amount of a compound to be tested to a reaction mixture. The reaction mixture contains the polynucleotide to be monitored for alterations in transcription. After transcription is allowed to occur, a transcription product is detected and measured to determine whether the amount of the transcription product has been altered by the compound.

A polynucleotide used in some aspects of the invention includes a promoter. A promoter is a polynucleotide to which an RNA polymerase binds such that a polynucleotide 3' (i.e., downstream) of, and operably linked to, the promoter is expressed. "Operably linked" refers to a juxtaposition wherein the components so described are in a relationship permitting them to function in their intended manner. Promoters of the invention typically include a core promoter element and an accessory. promoter element. A core promoter element includes a −10 sequence and a −35 sequence (see, for example, Hawley; D. K. et al (1983) *Nucl. Acids Res.* 11., 2237–2255). The first transcribed nucleotide is numbered +1. Nucleotides downstream of the transcription startpoint are consecutively numbered +2, +3, etc., and nucleotides upstream of the transcription startpoint are consecutively numbered −1, −2, etc.

The −10 sequence is typically about 6 nucleotides in length. The nucleotide sequence of the −10 sequence is typically made up of the nucleotides adenosine and thymidine, Preferably the nucleotide sequence of the −10 sequence is 5'-TATAAT. The −10 sequence is so named because the middle nucleotides of the −10 sequence are typically about 10 nucleotides upstream of the first transcribed nucleotide (i.e., the transcription startpoint). The last nucleotide of the −10 sequence (i.e., the 3' nucleotide) is typically at least about 6 nucleotides to no greater than about 9 nucleotides, preferably about 7 nucleotides, from the first transcribed nucleotide.

The −35 sequence of a core promoter is typically about 6 nucleotides in length. The nucleotide sequence of the −35 sequence is typically made up of the each of the four nucleosides. Preferably the nucleotide sequence of the −35 sequence is 5'-TTGACA. The −35 sequence is so named because the middle nucleotides of the −35 sequence are typically about 35 nucleotides upstream of the first transcribed nucleotide (i.e., the transcription startpoint). The last nucleotide of the −35 sequence (i.e., the 3' nucleotide) is typically at least about 27 nucleotides to no greater than about 38 nucleotides, preferably about 31 nucleotides, from the first transcribed nucleotide.

Core promoters that are identified by bacterial RNA polymerases can be used in the present invention. However, the particular core promoter is not critical to the practice of the present invention. Core promoters include, for instance, core promoters from eubacteria and from some bacteriophages. Nonlimiting examples of core promoters include the *E. coli* rrnb P1 core promoter, and the *E. coli* lac core promoter.

The accessory promoter element of the promoters useful in aspects of the invention are located 5' (i.e. upstream) of the core promoter. Surprisingly and unexpectedly, the accessory promoter elements of the present invention result in greatly enhanced transcription of polynucleotides, for instance transcription units, to which they are operably linked. There are three types of accessory promoter elements of the present invention: distal (i.e., relatively far from the first transcribed nucleotide), proximal (i.e., relatively close to the first transcribed nucleotide), and combined (i.e., contains both a distal accessory promoter element and a proximal accessory promoter element). Preferably, either a distal, a proximal, or a combined accessory promoter element is used in a promoter of the invention, more preferably, a proximal or a combined accessory promoter element, most preferably, a combined accessory promoter element.

A preferred example of a distal accessory promoter element has the nucleotide sequence 5'-NNAWWWWWTTTTTN (SEQ ID NO:4) or the complement thereof. Preferably, a distal accessory promoter element has the sequence of SEQ ID NOs:6–24 or 27, more preferably SEQ ID NOs:6, 27, or complements thereof. The last nucleotide of a distal accessory promoter element of SEQ ID NOs:4, 6–24, or 27 (i.e., the downstream nucleotide) is at least about 44 nucleotides, preferably at least about 45 nucleotides, from the first transcribed nucleotide. The last nucleotide of a distal accessory promoter element of SEQ ID NOs:4, 6–24, or 27 (i.e., the downstream nucleotide) is no greater than about 48 nucleotides, preferably no greater than about 47 nucleotides, from the first transcribed nucleotide. Most preferably, the last nucleotide of a distal accessory promoter element of SEQ ID NOs:4, 6–24, or 27 (i.e., the downstream nucleotide) is about 46 nucleotides from the first transcribed nucleotide.

A preferred example of a proximal accessory promoter element has the nucleotide sequence 5'-AAAAAARNR (SEQ ID NO:3) or the complement thereof. Preferably, a proximal accessory promoter element has the sequence of SEQ ID NOs:29–36, more preferably SEQ ID NOs:29–31, most preferably SEQ ID NO:29, or complements thereof. The last nucleotide of a proximal accessory promoter element of SEQ ID NOs:3 or 29–36 (i.e., the downstream nucleotide) is at least about 36 nucleotides, preferably at least about 37 nucleotides, from the first transcribed nucleotide. The last nucleotide of a proximal accessory promoter element of SEQ ID NOs:3 or 29–36 (i.e., the downstream nucleotide) is no greater than about 40 nucleotides, preferably no greater than about 39 nucleotides, from the first transcribed nucleotide. Most preferably, the last nucleotide of a proximal accessory promoter element of SEQ ID NOs:3 or 29–36 (i.e., the downstream nucleotide) is about 38 nucleotides from the first transcribed nucleotide.

A preferred example of a combined accessory promoter element has the nucleotide sequence 5'-NNAAAWWTWTTTTNNNAAANNN (SEQ ID NO:2) or the complement thereof. Preferably, a combined accessory promoter element is included in the present invention if it increases transcription of the *E. coli* rrnB P1 promoter core promoter element, not operably linked to a combined accessory promoter element, above the level that a wild type combined accessory promoter element increases transcription of the core promoter element. Transcription by the rrnB P1 core promoter (i.e., without a combined accessory promoter element) is determined using the promoter 66 to +1 CGCGGTCgactgcagtggtacctag-gaatCTTGTCAGGCCGGAATAACTCCCTATAATGC GCCACCA (SEQ ID NO:73). Nucleotides −37 to +1 of the *E. coli* rrnB P1 core promoter are shown as nucleotides 30 to 66 of SEQ ID NO:73. The nucleotides of SEQ ID NO:73 in lowercase are shown in FIG. 2 as SEQ ID NO:72. The increase in transcription by the wild type combined accessory promoter element is determined using the promoter −66 to +1 CGCGGTCagaaaattattttaaatttc-ctCTTGTCAGGCCGGAATAACTCCCTATAATGCG CCACCA (SEQ ID NO:74). The nucleotides of SEQ ID NO:74 in lowercase is the wild type combined accessory promoter element and are shown in FIG. 2 as SEQ ID NO:71. As described in Example 1, transcription by SEQ ID NO: 74 is about 69-fold higher than transcription by SEQ ID NO:73. Thus, a combined accessory promoter element of the present invention increases transcription of the rrnB P1 core promoter by greater than about 69-fold, more preferably at least about 100-fold, even more preferably at least about 200-fold, most preferably at least about 300-fold. A combined accessory promoter element of the present invention increases transcription of the rrnB P1 core promoter up to about 330-fold. The upper limit of an increase in transcription of other core promoters by a combined accessory promoter element is not known, and may be greater than 330-fold.

Preferably, a combined accessory promoter element has the sequence of SEQ ID NOs:1 or 40–70, more preferably SEQ ID NOs:1 or 40, most preferably SEQ ID NO:1. The last nucleotide of a combined accessory promoter element of SEQ ID NOs: 1 or 40–70 (i.e., the downstream nucleotide) is at least about 36 nucleotides, preferably at least about 37 nucleotides, from the first transcribed nucleotide. The last nucleotide of a combined accessory promoter element of SEQ ID NOs:1 or 40–70 (i.e., the downstream nucleotide) is no greater than about 40 nucleotides, preferably no greater than about 39 nucleotides, from the first transcribed nucleotide. Most preferably, the last nucleotide of a proximal accessory promoter element of SEQ ID NOs:1 or 40–70 (i.e., the downstream nucleotide) is about 38 nucleotides from the first transcribed nucleotide.

The present invention also provides polynucleotides including an accessory promoter element. The accessory promoter element has a nucleotide sequence of SEQ ID NOs:4, 6–24, or 27, preferably SEQ ID NOs:6, 27, or complements thereof, or a nucleotide sequence of SEQ ID NOs:3 or 29–36, more preferably SEQ ID NOs:29–31, most preferably SEQ ID NO:29, or complements thereof, or a nucleotide sequence of SEQ ID NOs:1–2 or 40–70, preferably SEQ ID NOs:1 or 40, most preferably SEQ ID NO:1, or complements thereof.

Preferably, a polynucleotide present downstream of, and operably linked to, a promoter of the invention contains a transcription unit. A "transcription unit" is a polynucleotide that is transcribed by an RNA polymerase that has bound to a promoter of the invention and initiated transcription. The 5' boundary of a transcription unit is generally determined by a transcription startpoint at its 5' end. A transcription startpoint is mainly defined by its spacing from the −10 sequence, −35 sequence, and accessory promoter element. The 3' boundary of a transcription unit is generally determined by a transcription terminator at its 3' end. Transcription terminators are known in the art.

Optionally and preferably, a transcription unit contains a coding region. A "coding region" is a polynucleotide that encodes a polypeptide and, when placed under the control of appropriate regulatory sequences expresses the encoded polypeptide. A regulatory region is a nucleotide sequence that regulates expression of a polynucleotide, for instance a transcription unit or a coding region, to which it is operably linked. The boundaries of a coding region are generally determined by a translation start codon at its 5' end and a translation stop codon at its 3' end. Nonlimiting examples of regulatory sequences that regulate expression of a polynucleotide, for instance a coding region, include the regulatory sequences that regulate expression of a transcription unit (for instance a promoter of the invention, a transcription startpoint, and a transcription terminator) as well as a ribosome binding site, translation start site (e.g., the codon ATG), and translation stop sites (e.g., UGA, UAG, and UAA). The term "polypeptide," as used herein, refers to a polymer of amino acids and does not connote a specific length of a polymer of amino acids. Thus, for example, the terms peptide, oligopeptide, protein, and enzyme are included within the definition of polypeptide, whether produced using recombinant techniques, chemical or enzymatic synthesis, or naturally occurring.

A promoter of the invention and operably linked transcription unit, coding region, and/or regulatory regions can be present on a vector. The term vector includes, but is not limited to, plasmid vectors, viral vectors, cosmid vectors, and artificial chromosome vectors. The vector can be integrated into a recipient bacterium's genome, or replicate autonomously in the cytoplasm. Preferably the vector is a plasmid. In some aspects of the invention preferably the recipient bacterium secretes minimal amounts of proteolytic enzymes. Suitable prokaryotes include eubacteria, such as gram-negative or gram-positive organisms, for example, *E coli, Bacilli* such as *B. subtilis, Pseudomonas* species such as *P. aeruginosa*, or *Salmonella* species such as *S. typhimurium*. Preferably, *E. coli* is used.

A polynucleotide that includes a promoter of the invention and a transcription unit can be inserted directly into a vector. Construction of vectors useful in the present invention employs standard ligation techniques known in the art. See, e.g., Sambrook et al, *Molecular Cloning: A Laboratory Manual.,* Cold Spring Harbor Laboratory Press (1989) or Ausubel, F. M., et al., ed. *Current Protocols in Molecular Biology*(1989). Suitable vectors include commercially available vectors such as pUC(X) and pET-(X), where (X) denotes a vector family in which numerous constructs are available. pUC(X) vectors can be obtained from Pharmacia Biotech (Piscataway, N.H.) or Sigma Chemical Co. (St. Louis, Mo.). pET-(X) vectors can be obtained from Promega (Madison, Wis.), Stratagene (La Jolla, Calif.), and Novagen (Madison, Wis.). Alternatively, a polynucleotide that includes an accessory promoter element of the invention can be inserted directly into a vector upstream of a core promoter already present in the vector.

A vector containing the promoter of the invention optionally includes one or more coding regions encoding a selectable marker, i.e., a molecule that inactivates or otherwise detects or is detected by a compound in the growth medium. For example, the inclusion of a coding region encoding a selectable marker can render a bacterium transformed with the vector resistant to an antibiotic, or it can confer compound-specific metabolism on the transformed cell. Non-limiting examples of selectable markers are those that confer resistance to kanamycin, ampicillin, chloramphenicol, tetracycline. Such marker sequences are well known in the art.

The reaction mixture of some aspects of the invention typically contains a polynucleotide that includes a promoter of the invention operably linked to a transcription unit and components that cause transcription of the polynucleotide. One of the components is at least one prokaryotic RNA polymerase that contains an α subunit. The at least one RNA polymerase can include a $\sigma^{70}$ subunit or a different σ subunit, preferably a $\sigma^{70}$ subunit. The C-terminal domain of the α subunit (αCTD) of RNA polymerases contains 7 amino acid residues that are highly conserved (i.e., >99%) between all eubacteria in which the amino acid sequence of the α subunit is known (Gaal, T. et al. (1996) *Genes Develop.* 10, 6–26). Thus, it is expected that RNA polymerases that contain an α subunit can be obtained from a variety of bacteria and can be used in the present invention. Moreover, it is expected that the identification of a compound that inhibits the ability of an RNA polymerase α subunit to interact with an accessory promoter element of the invention will also interfere with the ability of RNA polymerase α subunits present in other bacteria to interact with an accessory promoter element.

RNA polymerases useful in the present invention can be obtained from a bacterium by preparing a cellular extract. Methods for preparing cellular extracts are known in the art, see, e.g., Yang et al. (1979) *Proc. Natl. Acad. Sci. USA.* 76,3304–3308). Optionally, the RNA polymerase can be isolated or purified from a bacterium, see, e.g., Burgess R. R. et al. (1975) *Biochem.* 14, 4634–4638). Cellular extracts can be obtained by opening the cellular membrane of a bacterium under conditions that will decrease the likelihood of denaturation of polypeptides, preferably RNA polymerases, present in the bacterium. Methods of opening the cellular membrane of a bacterium are known in the art and can vary with the type of bacterium. Non-limiting examples include sonication and lysis with enzymes. Preferably, RNA polymerases useful in the present invention are obtained from, for instance, Promega (Madison, Wis.) or Epicentre (Madison, Wis.). Extracts containing RNA polymerase(s) and ribosomes are typically referred to as "S30 extracts."

The concentration of RNA polymerase and the concentration of salt in the final volume of the reaction mixture (i.e., the volume after all components of the reaction mixture have been added) is at a level such that the transcription product (either an RNA encoded by the transcription unit or a polypeptide encoded by the coding region) can be detected. Salts useful in the present invention include NaCl or KCl. Generally, the level of transcription by a promoter can be increased by increasing the concentration of RNA polymerase and/or decreasing the concentration of salt. Thus, a skilled person can determine the appropriate concentrations of RNA polymerase and salt to use by increasing the concentration of RNA polymerase and/or decreasing the concentration of salt until the transcription product (either an RNA encoded by the transcription unit or a polypeptide encoded by the coding region) can be detected. Examples of preferred lower final concentrations of an RNA polymerase (i.e., the concentration of an RNA polymerase in the final volume) are about 0.4 nM, more preferably about 4 nM. Examples of preferred higher final concentrations of an RNA polymerase are about 400 nM, more preferably about 40 nM. Examples of preferred lower final concentrations of a salt are at least about 50 mM, preferably about 100 mM, more preferably about 150 mM, even more preferably about 160 mM. Examples of preferred higher final concentrations of a salt are about 200 mM, preferably about 190 mM, more preferably 20 about 180 mM.

In addition to an RNA polymerase, other components that can be optionally used include, for example, at least one buffer, at least one salt, and rNTPs. If a polypeptide is to be produced, the reaction mixture can also contain components necessary for translation, including, for example, amino acids, tRNAs, ribosomes, and factors including initiation and elongation factors. Other components of the reaction mixture can include other polypeptides and/or reducing agents that stabilize RNA polymerases and/or ribosomes. Preferably, a reaction mixture includes a cellular extract.

In some aspects of the present invention, the resulting product of transcription (i.e., an RNA polynucleotide) or subsequent translation (i.e., a polypeptide) of a polynucleotide operably linked to a promoter of the invention is preferably detected. Methods to detect RNA polynucleotides and polypeptides are known in the art. For example, the presence of an RNA polynucleotide or a polypeptide can be detected by resolving on a gel, for instance an agarose or polyacrylamide gel, a mixture containing the RNA polynucleotide or a polypeptide. After staining the gel using methods known in the art, the presence or absence of the RNA polynucleotide or a polypeptide on the gel can be determined.

Methods are known that increase the ability to detect RNA polynucleotides and polypepitdes. For instance, a polypeptide resolved on a gel can be detected using an antibody that binds to the polypeptide and then detecting the antibody. Transcription or translation can occur in the presence of a detectable label, for instance a labeled rNTP or a labeled amino acid (i.e., the labeled rNTP or a labeled amino acid can be added to the reaction mixture). The detectable label can be a radioactive label, a fluorescent label, an enzymatic label, or a combination thereof. The detectable label is typically incorporated in an rNTP or an amino acid by having the label attached thereto. Radioactive labels preferably include those radioactive labels that are beta, gamma emitters and even alpha emitters, more preferably radioactive labels are $P^{32}$, $P^{33}$, $S^{35}$, or $I^{125}$, to name a few. Fluorescent labels are typically dye labels that emit visible radiation in passing from a higher to a lower electronic state, typically in which the time interval between absorption and emission of energy is relatively short, generally on the order of about $10^{-8}$ to about $10^{-3}$ second. Suitable fluorescent labels can include fluorescein, rhodamine, and luciferin, to name a few. Suitable enzymatic labels that can be utilized in accordance with the present invention include, for example, horse radish peroxidase, alkaline phosphatase, and other enzymes that under appropriate conditions generate a color reagent. Enzymatic labels often can also be detected using an antibody that binds the enzyme.

Alternatively, the coding region can encode a detectable marker. Non-limiting examples of detectable markers that can be used to detect expression of a coding region include β-galactosidase, luciferase, green fluorescent protein, and chloramphenicol acetyl transferase, each of which are known in the art.

The compounds added to a reaction mixture can be a wide range of molecules and is not a limiting aspect of the invention. Compounds include, for instance, a polyketide, a non-ribosomal peptide, a polypeptide, or other organic molecules. Generally, a compound alters transcription by a promoter of the invention by altering the ability of an RNA polymerase to interact with an accessory promoter element and subsequently initiate transcription. Preferably, a compound decreases the ability of an RNA polymerase, preferably the a subunit, to interact with an accessory promoter element, and thereby decreases transcription. A non-limiting example of how a compound may act includes binding to at least a portion of the accessory promoter element, optionally including at least a portion of the promoter that is not part of the accessory promoter element, such that the ability of RNA polymerase to interact with the promoter is altered. For example, a compound may bind to the small groove or the large groove of at least a portion of a series of adenine residues (i.e., an A-tract) of the accessory promoter element. Another non-limiting example of how a compound may act includes the binding of a compound to an RNA polymerase subunit, or the modification of an RNA polymerase subunit by a compound, such that the ability of RNA polymerase to interact with the accessory promoter element is altered. Preferably the RNA polymerase subunit is an α subunit. It is expected that compounds identified by the methods of the invention will inhibit bacterial growth and thus can be used as antibiotics.

Typically, whether a compound alters transcription of a promoter of the invention can be measured by assessing two variables. The first variable is whether the amount of the transcription product in the presence of the compound is altered relative to the amount of the transcription product in the absence of the compound. Preferably, the amount of transcription product is altered in the presence of the compound. The second variable is whether the compound alters transcription of a second promoter that has the same core promoter element but lacks the accessory promoter element. The second promoter is operably linked to a transcription unit, preferably the same transcription unit that is operably linked to the promoter of the invention. Preferably, the amount of transcription product from the second promoter is not altered in the presence of the compound.

The present invention also provides kits for testing the ability of a compound to alter, preferably decrease, transcription of a transcription unit. Preferably, the transcription unit includes a coding region as described herein. However, the particular transcription unit or coding region is not critical to the practice of the present invention. Such a kit includes a polynucleotide that includes a promoter of the invention. The promoter is operably linked to a transcription unit and the promoter includes an accessory promoter element and a first core promoter element as described herein. Preferably the polynucleotide is present on a plasmid vector. The polynucleotide that includes a promoter of the invention can be added to a reaction mixture containing the compound to be tested. Optionally, a kit of this aspect of the invention also includes an additional polynucleotide that includes a second promoter operably linked to a transcription unit. This second promoter has the first core promoter element but lacks the accessory promoter element. Preferably, a compound alters transcription initiated by a promoter that contains an accessory promoter element and does not alter transcription of a promoter that does not include the accessory promoter element.

The present invention also provides methods of determining whether a bacterium produces a compound that alters transcription, preferably decreases transcription, of a polynucleotide. A polynucleotide that included a promoter of the invention operably linked to a transcription unit can be introduced to a bacterium. The promoter includes an accessory promoter element and first core promtoer. The amount of a transcription product can be detected and compared to the amount of a transcription product from second promoter. The second promoter includes the first core promoter but does not include the accessory promoter element. It is expected that a bacterium that causes altered levels of transcription from a promoter that includes an accessory promoter element compared to a promoter that does not contain the accessory promoter element produces a compound that alters transcription of a promoter of the invention.

The polynucleotide is typically present on a vector, preferably a plasmid vector. A variety of techniques are available for the introduction of the polynucleotide into a bacterium. However, the particular manner of introduction of the polynucleotide to the bacterium is not critical to the practice of the present invention, and methods which provide for efficient transformation may be employed. Transformation of bacterial host cells can be accomplished by methods known in the art and include, for instance, electroporation or calcium chloride treatment.

A compound identified in this method can be isolated using protein purification methods known in the art. The following are non-limiting examples of suitable protein purification procedures: fractionation on ion-exchange, hydroxyapatite, Phenyl-Sepharose HP, Q sepharose, Mono P, Mono Q, and Mono S columns; acetone precipitation and/or ethanol precipitation; reverse phase HPLC; chromatography on silica or on an ion-exchange resin such as DEAE; chromatofocusing; SDS-PAGE; ammonium sulfate precipitation; and gel filtration using, for example, Sephadex G-75.

The present invention also provides methods directed to producing an RNA polynucleotide. Such methods include introducing to a bacterium a polynucleotide that includes a promoter of the invention operably linked to a transcription unit, incubating the bacterium under conditions that promote expression of the transcription unit, and isolating the RNA polynucleotide. The promoter includes an accessory promoter element and a core promoter element. The particular transcription unit is not critical to the practice of the present invention.

Examples of RNA polynucleotides include, for instance, RNA polynucleotides that act as structural RNAs, antisense RNAs, or catalytic RNAs including ribozymes. RNA polynucleotides can be purified using methods known in the art, including, for example, preparative gel electrophoresis or hybridization methods. Optionally, the transcription unit can include a coding region. Typically, when the transcription unit includes a coding region the methods are directed to producing a polypeptide. The particular coding region is not critical to the practice of the present invention.

Polypeptides can be isolated using methods known in the art, as described herein. Optionally, a coding region can be altered by inserting a series of nucleotides in frame with the coding region, such that the resulting fusion polypeptide contains a polypeptide fused to an additional domain. This can be used to introduce domains that can facilitate the isolation of the polypeptide. For instance, domains useful in the isolation of a fusion polypeptide include a histidine domain (which can be isolated using nickel-chelating resins) and an S-peptide domain (which can be isolated using an S-protein) (available from Invitrogen, Carlsbad, Calif., and Novagen, Madison, Wis.),. Domains useful in targeting a polypeptide to the exterior surface of a cell can also be introduced. For instance, domains useful in targeting a polypeptide include bacterial signal sequences.

The present invention also provides kits for expressing an RNA polynucleotide. The kit includes a polynucleotide that includes a promoter of the invention and at least one restriction endonuclease site. The promoter typically includes an accessory promoter element and a core promoter element. The restriction endonuclease site can be used to insert a transcription unit 3' of the promoter. Typically, the at least one restriction endonuclease site is located at a distance 3' of the promoter such that an inserted transcription unit is located the proper distance from the core promoter element and the accessory promoter element for transcription initiation. Optionally, the transcription unit includes a coding region. Typically, when the transcription unit includes a coding region the kit can be used to express a polypeptide. The particular transcription unit or coding region is not critical to the practice of the present invention.

The polynucleotide of the kit can be present in a vector, preferably a plasmid vector. The polynucleotide can be introduced to a bacterium as described herein, and the bacterium subsequently incubated under conditions that cause expression of the transcription product. Alternatively, the polynucleotide can be incubated in a buffer suitable for allowing transcription, and optionally, translation, to occur. Such buffers are described herein.

The present invention is illustrated by the following examples. It is to be understood that the particular examples, materials, amounts, and procedures are to be interpreted broadly in accordance with the scope and spirit of the invention as set forth herein.

EXAMPLE 1

Identification of an UP Element Consensus Sequence for Prokaryotic Promoters

This Example presents the identification of accessory promoter elements, located upstream of an *E. coli* core promoter, that increase promoter activity by as much as 326-fold. These accessory promoter elements are referred to as "UP elements" in Example 1 and Example 2. This Example also demonstrates that the identified accessory promoter elements interact with the α subunit C-terminal domain (αCTD) of RNA polymerase.

Materials and Methods rrnB P1 Promoter Fragments with Random Upstream Sequences. An in vitro selection was used to identify sequences from a random DNA population fused upstream of the rrnB P1 −35 hexamer that would increase the rate of formation of complexes with RNAP (FIG. 1). The procedure was modeled after selections for binding sites for other proteins (Pollock, R. et al.(1990) *Nucl. Acids Res.* 18, 6197–6204; Tuerk, C. et al.(1990) *Science* 249, 505–510; Blackwell, T. K. et al. (1990) *Science* 250, 1104–1110; Wright, W. E. et al. (1991) *Mol. Cell. Biol.* 11, 4104–4110). In addition, the incubation time of the DNA fragments with RNAP was limited to enrich for promoters that bound RNAP rapidly. RNAP holoenzyme was used, rather than the purified α subunit of RNAP holoenzyme, so that the selected sequences would be positioned correctly with respect to the rest of the promoter to increase the rate of formation of complexes with RNAP. Correct alignment of upstream sequences with respect to the core promoter is important for proper function Lisser, S. (1993) *Nucl. Acids Res.* 21, 1507–1516; Newlands, J. T. et al. (1992) *Nucl. Acids Res.* 20, 719–726; Bracco, L. et al. (1989) *EMBO J.* 9, 4289–4296; McAllister, C. F. et al. (1989) *J. Biol. Chem.* 264, 10451–10456).

Figure 1B:
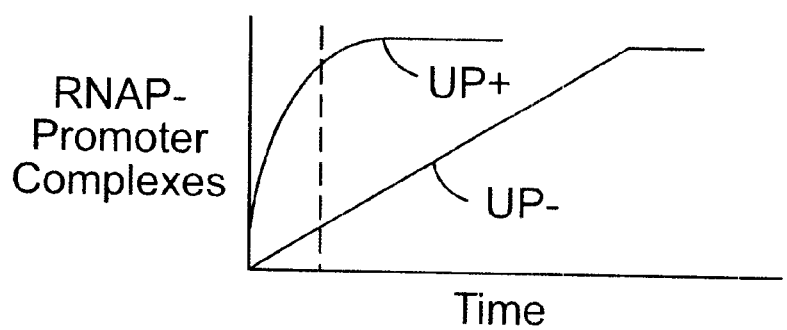

Promoter fragments used in the -first round of selection were synthesized in vitro from two partially complementary oligonucleotides (FIG. 1A). The top strand oligonucleotide (80 nucleotides) contained (from 5' to 3') an EcoRI site (RI), rrnB P1 sequence from −66 to −60, random sequence from −59 to −38 indicated as "N", and rrnB P1 sequence from −37 to +1. The designation of a nucleotide as +1 indicates that the nucleotide is the transcription start site. The designation of a nucleotide with a minus sign or a plus sign indicates the position of the nucleotide relative to the transcription start site: a nucleotide preceded by minus sign is located 5' of transcription start site and a nucleotide preceded by plus sign is located 3' of transcription start site. The bottom strand oligonucleotide (81 nucleotides) contained (from 5' to 3') a HindIII site (H3) and rrnB P1 sequence from +50 to −17. Each contained a short additional sequence 5' to the restriction site to ensure enzyme digestion. The sequence of the top strand oligonucleotide was 5'-GACGTCAGGAATTCCGCGGTCNNNNNNNNN NNNNNNNNNNNNNCTTGTCA GGCCGGAATAACTC- CCTATAATGCGCCACC (SEQ ID NO:82), and the sequence of the bottom strand oligonucleotide was 5'-GTCGAAGCTTGGTCAGGAGAACCCCGCTGACC CGGCGGCGTGTTTGCCGTT GTTCCGTGTCAGTG- GTGGCGCATTATAGGG (SEQ ID NO:83). Oligonucleotides were annealed and extended with T7 DNA polymerase to form a library of double stranded DNA fragments with different UP element regions (−59 to −38). Oligonucleotides (2.4 ng each; Genosys Biotechnologies, The Woodlands, Tex.; NSC Technologies, Mt. Prospect, Ill.) were incubated in 40 mM Tris-HCl (Cat. No. T-1503, Sigma, St. Louis, Mo.), pH 7.5, 20 mM $MgCl_2$, 50 mM NaCl for 5 min at 95° C., then annealed by slow cooling to 30° C. The 3' ends were extended with 0.5 mM dNTPs and T7 DNA polymerase (Sequenase, Amersham, Piscataway, N.J.) at 37° C. for one hour, and the resulting fragments were extracted with phenol, then chloroform, and dNTPs were removed using a Microcon 30K filter (Amicon, Beverly, Mass.). Eighteen randomly chosen fragments were sequenced after cloning into phage λ as described by Gourse, R. L. et al. (1986) *Cell* 44, 197–205; the frequency of each base at each position in the randomized region (−59 to −38) was approximately equal. The entire population of promoter fragments (1 µg) was digested with HindIII and labeled with 5 µCi α[$^{32}$P]-dATP and T7 DNA polymerase for 15 minutes at 37° C. in NEBuffer 2 (New England Biolabs, Beverly, Mass.).

In vitro Selection. RNAP (obtained from R. Landick, University of Wisconsin, Madison) was isolated from *E. coli* strain MRE600 by the method of Burgess R. R. et al. (1975) *Biochem.* 14, 46344638. Labeled promoter fragments were incubated with 4 nM RNAP in 30 mM KCl, 10 mM Tris-Cl pH 7.9, 10 mM $MgCl_2$, 1 mM DTT, 0.1 mg/ml BSA, 500 µM ATP, 50 µM CTP for 4 minutes at 22° C., followed by addition of 10 µg/ml heparin (Cat. No. H-3125, Sigma). The initial round of selection contained approximately $7 \times 10^{12}$ promoter DNA fragments, representing about 40% of the $4^{22}$ possible upstream sequence combinations.

RNAP-promoter complexes were separated from unbound DNA on 5% nondenaturing polyacrylamide gels, eluted by diffusion into Tris-HCl (10 mM)- ethylenediaminetetraacetic acid (EDTA) (1 mM), pH 8.0, and then purified by using a Centrex UF-0.5 spin filter (Cat. No. 77761, Schleicher & Schuell, Keene, N.H.). The purified DNA was amplified by PCR using Pfu DNA polymerase (Stratagene, La Jolla, Calif.) and a downstream primer (5'-GTCCAAGCTTGGTCAGGAGAACCCCGCT- GACCCGGCGGCGTGTTFGCCGTTGTTC- CGTGTCAGTGGTGGCGCATTATAGGGAGTTATT CCGGCCTGACAAG (SEQ ID NO:88) and an upstream primer (5'-GACGTCAGGAATTCCGCGG) (SEQ ID NO:89). Primers were obtained from Integrated DNA Technologies (Coralville, Iowa) or NSC Technologies, and contained all nonrandomized promoter positions to reduce the frequency of PCR-generated mutations that might increase core promoter binding by RNAP. The downstream primer contained a HindIII site and rrnB P1 sequence from +50 to −37, and the upstream primer contained an EcoR1 site and rrnB P1 sequence from 66 to −60. PCR conditions were as follows: 20 mM Tris-Cl pH 8.75, 2.5 units Taq polymerase, 10 mM KCl, 10 mM ammonium sulfate, 10 mM $MgSO_4$, 0.1% Triton X-100, 100 µg/ml bovine serum albumin, 250 µM dNTPs, 0.1 µg of the upstream primer and 0.4 µg of the downstream primer, in a total volume of 110 µl; 15 cycles of 95° C. for 5 minutes, 53.5° C. for 1 minute, 72° C. for 1 minute. PCR reactions were monitored after 10–14 cycles of amplification in order to avoid heteroduplexes (resulting from annealing of noncomplementary products). Samples of PCR reactions were resolved on a gel, and the PCR reactions stopped before heteroduplexes could become a significant component in the population (Pollock, R. et al. (1990) *Nucl. Acids Res.* 18 6197–6204). The second and subsequent rounds of selection used PCR-amplified promoter fragments from the previous round, and the RNAP binding reactions were carried out under progressively more stringent conditions (RNAP concentrations were decreased from about 4 nM to about 0.4 nM, and reaction times were decreased from about 4 minutes to about 1 minute). Twenty-four rounds of in vitro selection were performed, and the most active promoters in vivo (see below) were sequenced after rounds 5, 9, 14, 19, 22, and 24.

In vivo Activity Determination. PCR-amplified promoter fragments were digested with EcoRI and HindIII and ligated to purified arms of phage λ (see Gourse, R. L. et al. (1986) *Cell* 44 197–205) to construct hybrid promoter-lacZ fusions (Miura, A. et al. (1981) *Cell* 25, 773–782, Gaal, T. et al. (1989) *J. Bacteriol.* 171, 4852–4861). Hybrid promoter-lacZ fusions were also constructed using the wild-type rrnB P1 promoter (i.e., bases −66 to +50, which includes the natural UP element sequence from −59 to −38, as described in Ross, W. et al. (1993) *Science* 262, 1407–1413 and the core rrnB P1 promoter. The core rrnB P1 promoter was identical to the wild-type rrnB P1 promoter, but it contained an upstream sequence with no UP element function. Phage DNAs were packaged in vitro as described by Gourse, R. L. et al. ((1986) *Cell* 44, 197–205), and phage were plated on *E. coli* NK5031 on pH 6 MacConkey agar plates containing 3% lactose (Gaal, T. et al. (1989) *J. Bacteriol.* 171, 4852–4861).

Promoter DNAs from phage producing dark red plaques [i.e. higher β-galactosidase activity than from the wild-type rrnB P1 promoter] were identified. Fifty percent to sixty percent of the fusions exhibited plaque phenotypes stronger than wild type rrnB P1, and lysogens were constructed from 31 of these phages (24 from round 24 and 7 from round 19). Lysogens were constructed as described by Gourse, R. L. et al. ((1986) *Cell* 44, 197–205). Strains monolysogenic for λ prophages carrying the promoter-lacZ fusions were distinguished from multi-lysogens by a PCR-based assay described previously by Powell, B. S. et al. ((1994) *Nucl. Acids Res.* 22, 5765–5766).

β-galactosidase activities were measured from cells grown in LB (Miller, J. H. (1972) In: *Experiments in molecular genetics,* Cold Spring Harbor Laboratory, Cold Spring Harbor, N.Y. pp. 352–355; Gaal, T. et al. (1989) *J. Bacteriol.* 171, 4852–4861). β-galactosidase activities of the 31 strains containing the promoter fragments fused to lacZ were compared with those from rrnB P1 promoter-lacZ fusions containing or lacking the natural rrnB P1 UP element (i.e., the wild-type rrnB P1 promoter and the core rrnB P1 promoter, respectively). All 31 promoters were more active in vivo than the natural rrnB P1 promoter (FIG. 2A). The upstream sequence with the greatest effect, 4192, increased transcription 326-fold, about 5-fold more than the rrnB P1 UP element.

Upstream Consensus Sequence. The sequences of the 31 upstream regions (FIG. 2A) share common features. All are A+T rich (64–91%), and most contain two A-tracts (i.e., 3 to 6 adenine bases) and an intervening T-tract (i.e., 3 to 9 thymidine bases). As illustrated in the frequency distribution (FIG. 2B), almost all have A residues at positions −41 to −43, and greater than 50% have A at position −44. In addition, nearly all contain A residues at −56 and −57, and 81% contain an A at −55. Nearly all contain a T-tract from −47 to −50 and A or T residues between −51 and −54. Positions −38 to −40 contain only 8 of the 64 possible triplets, suggesting that there are also constraints for UP element function at these positions.

Lac and Hybrid-lac Promoters. A representative selected upstream sequence (4192; FIG. 2A) was fused to a different core promoter, lac, to determine whether the 4192 element would increase transcription from other promoters. Strains containing lac or hybrid-lac promoters (Table 1) were derivatives of NK5031 containing promoter-lacZ fusions constructed in λ phage system II (Rao, L. et al. (1994) *J. Mol. Biol.* 235, 1421–1435). The rrnB P1-lac hybrid promoter present in strain 4282 was described previously (Rao, L. et al. (1994) *J. Mol. Biol.* 235, 1421–1435). Strain RLG 4288 contained nucleotides −40 to +52 of the lac promoter and gene. Nucleotides −40 to −1 of the lac promoter were 5'-AGGCTTTACAClMATGCTTCCGGCTCGTATGTT GTGTGG (SEQ ID NO:84), and no UP element. Strain RLG 4208 contained a fusion between 4192 and nucleotides −37 to +52 of the lac promoter and gene. The 4192-lac hybrid promoter contained (from 5' to 3') an EcoRI site, rrnB P1 sequence from −66 to −60, upstream sequence 4192 from −59 to −38, and lac promoter sequence from −37 to +52.

TABLE 1

Effects of upstream sequences on lac core promoter activity

| Strain | Promoter | Miller Units** | Relative Activity |
|---|---|---|---|
| RLG 4288 | lac (−40 to +52)* | 50 | 1 |
| RLG 4208 | 4192-lac hybrid | 5390 | 108 |
| RLG 4282 | rrnB P1-lac hybrid | 1940 | 39 |

*The sequence from position −59 to −38 in this construct is 5'-gac tgc agt ggt acc tag gag g (SEQ ID NO:5). This nucleotide sequence does not function as an UP element.
**Average activity (two experiments with less than 2% variability).

Upstream sequence 4192 increased transcription from the lac core promoter 108-fold in vivo, greater than the 39-fold effect of the rrnB P1 UP element on the lac core promoter (Table 1), consistent with the relative effects of the two upstream sequences on the rrnB P1 core promoter (FIG. 2). The two upstream sequences increased transcription of rrnB P1 slightly more than lac (FIG. 2), reflecting differences in the kinetic characteristics of, and/or sequences of, positions −39 and −38 in the two core promoters (Table 1). It has been proposed previously that upstream sequences can confer different effects on promoters with different kinetic characteristics (Ellinger, T. et al. (1994) *J. Mol. Biol.* 239, 466475; Tang, Y. et al. (1996) *J. Bacteriol.* 178, 6945–6951).

In vitro Transcription. In vitro transcription of the rrnB P1 core promoter, the rrnB P1 promoter with its natural UP element (wild type rrnB P1), and the rrnB P1 promoter with upstream sequence 4192 was compared. Promoter fragments were cloned into pRLG770 (Ross, W. et al. (1990) *EMBO J.* 92 3733–3742). Plasmids were transcribed with wild type RNA polymerase (WT RNAP) and two other RNA polymerases (αΔCTD RNAP, which lacks the αCTD of the α subunit, or αR265A RNAP, which contains an alanine substituted at position 265 of α domain) in order to determine whether this transcription was dependent on the DNA binding domain of the RNAP a subunit.

Supercoiled DNA concentrations were determined both spectrophotometrically and by quantitation of the amount of RNA-1 transcription (an RNA made by ColE1 plasmids) under conditions of RNAP excess (40 nM). Transcription was carried out as described (Ross, W. et al. (1993) *Science* 262 1407–1413) except that reactions contained 170 mM NaCl. Reconstituted RNAPs (Gaal, T. et al. (1996) *Genes Dev.* 10, 16–26, Tang, H. et al. (1996) *Meth. Enzymol.* 273, 130–134) were used at concentrations that resulted in equivalent transcription from the lacUV5 promoter (2.7 nM for WT RNAP, 9 nM for αR265A RNAP, and 17.4 nM for αΔCTD RNAP). Reconstituted RNAPs are RNAPs assembled in vitro from purified α, β, β', and σ subunits (Tang, Y. et al. (1996) *Methods Enzymol.* 273, 130–134). The lacUV5 promoter had the sequence (−64 to −1) 5'-GAATTCTCACTCATTAGGCACCCCAGGCTTT ACACTTTATGCTTCCGGCTCGTATAATGTGTGG (SEQ ID NO:85). Transcription products were resolved by gel electrophoresis on a 5% acrylamide-7% urea gel. Gels were analyzed by phosphorimaging (Molecular Dynamics).

Like the wild type rrnB P1 UP element, upstream sequence 4192 stimulated transcription in the absence of factors other than RNAP, and it had a greater effect than the wild type rrnB P1 UP element, consistent with the relative effects of the two sequences n vivo.

As with the wild type rrnB P1 UP element, upstream sequence 4192 increased transcription only with RNAP containing the wild type αCTD. Upstream sequence 4192 therefore has the characteristics of an UP element.

Footprinting. DNase I footprinting was used to determine whether UP element 4192 was protected by RNAP, and whether the interaction was dependent upon amino acid residue R265 in α, as was observed for the rrnB P1 UP element (Ross, W. et al. (1993) *Science* 262, 1407–1413; Gaal, T. et al. (1996) *Genes Dev.* 10, 16–26). [Since DNAse I cleaves A+T-rich sequences inefficiently, only a subset of UP element positions could be monitored for RNAP binding.] Promoter fragments were generated by PCR from plasmids pRLG4238 (rrnB P1) or pWR68 (4192-rrnB P1) using the vector-specific primers 5'-CCGCGGATCCGTATCACGAGGCCCTTTCG (SEQ ID NO:75) and 5'-GCGCTACGGCGTTTCAGTTC (SEQ ID NO:76). PCR conditions were as follows: 10 ng plasmid DNA, 2.5 units Taq polymerase, 10 mM Tris-Cl, pH 9.0, 50 mM KCl, 0.1% Triton X-100, 500 µM each dNTP, and 0.4 µg of each primer; 25 cycles of 95° C. for 1 minute, 45° C. for 1 minute, 72° C. for 2 minutes. The amplified promoter fragments were digested with HindIII (at position +50) and end-labeled with α[$^{32}$P]dATP (DuPont) (Newlands, J. T. et al. (1991) *J. Mol. Biol.* 220, 569–583). Labeled fragments were purified on 5% acrylamide-7 M urea gels to eliminate nicked DNAs, eluted by diffusion, purified using an Elutip (Schleicher and Schuell), incubated at 95° C. for 4 minutes in 20 mM NaCl, 20 mM Tris-HCl, 1 mM EDTA, pH 7.4, and reannealed at 65° C. for 30 minutes followed by slow cooling to 30° C. Footprints were performed essentially as described (Ross, W. et al. (1993) *Science* 262, 1407–1413; Gaal, T. et al. (1996) *Genes Dev.* 10, 16–26; Newlands, J. T. et al. (1991) *J. Mol. Biol.* 220, 569–583). DNase I footprint reactions were done at 37° C. with 59 nM wild-type or 82 nM αR265A RNAP. Both the core promoter region and positions −46, −47, −59 and −60 in UP element 4192 were protected by wild-type RNAP. The evidence suggests that the αCTD is required for binding of RNAP to UP element 4192.

In order to determine in finer detail the positions of the promoters protected by wild type RNAP or purified α subunit, hydroxyl radical footprint reactions were done at 22° C. with 16 nM wild-type RNAP or 5 µM α, purified as described by Tang, Y. et al. ((1996) *J. Bacteriol.* 178, 6945–6951). Gels were analyzed by phosphorimaging. Both RNAP and the α subunit protected regions centered at about −40 and −51 in each UP element. This evidence suggests that the 4192 UP element interacts with α similarly to previously characterized UP elements.

Example 2

Subsite Structure of UP Elements

This Example demonstrates that UP elements include a proximal subsite and a distal subsite. Each subsite constitutes a binding site for a single copy of αCTD.
Materials and Methods Synthesis of promoter populations containing randomized proximal or distal upstream sequences. rrnB P1 promoter fragments used in the first round of in vitro selection were synthesized by annealing partially complementary top and bottom strand oligonucleotides and by using T7 DNA polymerase as described herein. Oligonucleotides were purchased from Integrated DNA Technologies (Coralville, Iowa) or the University of Wisconsin Biotechnology Center, or were donated by NSC Technologies (Mt. Prospect, Ill.). The top strand oligonucleotide contained random sequences in either the proximal or distal UP element subsite. The oligonucleotide with a random proximal subsite contained (from upstream to downstream) an EcoRI site, rrnB P1 sequence from −66 to −60, 5'-GACTGCAGTGGTA-3' from −59 to −47 (these sequences replaced the distal subsite with sequences that do not influence transcription), random bases from −46 to −38, and rrnB P1 sequence from −37 to +1 (see also FIG. 3). The nucleotide sequence of this oligonucleotide was 5'-GACCTCAGGAATTCCGCGGTCGACTGCAGTG GTANNNNNNNNNCTTGTCAGGCCG-GAATAACTCCCTATAATGCGCCACC (SEQ ID NO:86). The oligonucleotide with a random distal subsite contained an EcoRI site, rrnB P1 sequence from −66 to −60, random bases from −59 to −46, 5'-CTAGGAAT-3' from −45 to −38 (these sequences replaced the proximal subsite with sequences that do not influence transcription), and rrnB P1 sequence −37 to +1 (see also FIG. 4). The nucleotide sequence of this oligonucleotide was 5'-GACGTCAGGAATTCCGCGGTCNNNNNNNNN NNNNNCTAGGAATCTFGTCAGGCCG-GAATAACTCCCTATAATGCGCCACC (SEQ ID NO:87). The bottom strand oligonucleotide for synthesizing both promoter populations contained a HindIII site and rrnB P1 sequence from +50 to −17. The nucleotide sequence of the bottom strand oligonucleotide used to identify proximal subsite sequences and to identify distal subsite sequences was 5'-GTCGAAGCTTGGTCAGGAGAACCCCGCTGA CCCGGCGGCGTGTTTGCCGTTG TTCCGTGT-CAGTGGTGGCGCATTATAGGG (SEQ ID NO:83). Seventeen proximal and 8 distal promoter fragments were sequenced without selection after cloning into phage λ to confirm that the frequencies of each of the 4 bases in the random regions were approximately equal.

UP element selection and screen. The selection was modeled after previous in vitro selections for protein binding sites on nucleic acids (Blackwell, T. K. et al. (1990) *Science* 250, 1104–1110; Pollock, R. et al. (1990) *Nucleic Acids Res.* 18 6197–6204; Tuerk, C. et al. (1990) *Science* 249, 505–510; Wright, W. E. (1991) *Mol. Cell Biol.* 11 4104–4110). In the first round of selection, radioactively-labeled promoter fragments (0.5 µg; approximately 3×10$^{12}$ DNA molecules, which was in excess of the 5×10$^6$ or 6.4×10$^9$ molecules needed to ensure that all sequence combinations were represented in the 9 positions of the proximal subsite or the 14 positions of the distal subsite selections, respectively) were incubated with RNAP for 4 minutes, and bound fragments were separated from unbound by gel electrophoresis as described herein. For the second and subsequent rounds of selection, promoter fragments were amplified by PCR from gel-isolated RNAP-promoter complexes as described herein. The PCR primers contained all of the nonrandomized promoter positions to reduce the frequency of PCR-generated mutations in the core promoter region that might increase binding by RNAP as described above. The PCR primers used for proximal subsite selection were 0.1 µg of 5'-GACGTCAGGAATTCCGCGGTCGACTGCAGTGGTA (SEQ ID NO:77) and 0.4 µg of 5'-GTCCAAGCTTGGTCAGGAGAACCCCGCTGA
CCCG
(iCGGCGGTGTGCCGTTGTTCCGTGTCAGTGGTG
GCGCATTATAGGGAGTTATTCCGGCCTGACAAG
(SEQ ID NO:73). The PCR primers used for distal subsite selection were 0.1 μg of 5'-GACGTCAGGAATTCCGCGGTC (SEQ ID NO:78) and 0.4 μg of 5'-GTCCAAGCTTGGTCAGGAGAACCCCGCTGACC
CGGCGGCGTGTTTGCCGTTGTTCCGTGT-
CAGTGGTGGCGCATTATAGGGAGTTAT-
TCCGGCCTGACAAGATTCCTAG (SEQ ID NO:79). PCR conditions were as follows: 20 mM Tris-Cl pH 8.75, 2.5 units Taq polymerase, 10 mM KCl, 10 mM ammonium sulfate, 10 mM $MgSO_4$, 0.1% Triton X-100, 100 μg/ml bovine serum albumin, 250 μM dNTPs, and the appropriate primer pair, in a total volume of 110 μl; 15 cycles of 95° C. for 5 minutes, 53.5° C. for 1 minute, 72° C. for 1 minute. RNAP binding reactions were carried out under progressively more stringent conditions as disclosed above. The progress of the selection was monitored by sequencing representatives of the selected populations following 8 (for the proximal) and 6 (for the distal) rounds of selection. A total of 13 cycles of RNAP binding, separation on gels, and PCR were carried out for each selection.

In vitro selected promoters were fused to lacZ in phage λ and screened for high promoter activity on MacConkey lactose indicator plates as described above. The promoter regions of the selected lacZ fusions were sequenced after PCR of DNA obtained directly from plaques as described in Example 1. Three promoters from the proximal subsite selection and 9 from the distal subsite selection were discarded, because they contained deletions or core promoter mutations. β-galactosidase activities were determined from monolysogens of strain NK5031 that had grown exponentially at least three generations in Luria-Bertani medium (LB; Ross, W. et al. (1998) *J. Bacteriol.* 180, 5375–5383).

Identification of Optimal Proximal Subsite Sequences

Based on plaque color, at least 90% of the selected proximal subsite promoters were more active than the control promoter lacking an UP element, and remarkably, about 30% were even more active than the wild-type rrnB P1 promoter.

Figures 3A, 3B, 3C:
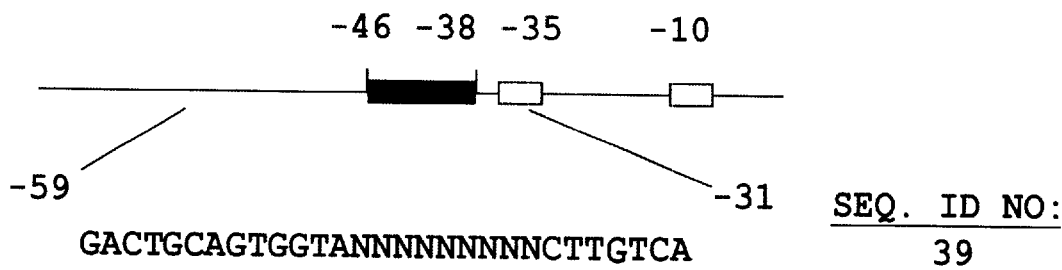
FIG. 3. Proximal subsites. Sequences and relative activities of 8 promoters selected for binding of RNAP in vitro and screened for high transcription in vivo. A. DNA fragments contained a wild-type rrnB P1 core promoter sequence (open boxes indicate the −10 (TATAAT) and −35 (TTGTCA) elements), a distal region (−59 to −47) that does not influence transcription, and different proximal region sequences (−46 to −38, filled rectangle) derived from a random sequence library. The randomized residues are indicated as "N" and are shown in context below the schematic in B. The −35 hexamer is in boldface. B. Proximal subsite sequences (i.e., proximal accessory promoter elements) are shown for the 8 promoters, for an rrnB P1 construct containing only the proximal subsite of the rrnB P1 UP element ("rrnB P1 proximal"; RLG3098), and for a construct lacking an UP element ("No UP"; RLG3097). The names refer to the strain numbers of λ lysogens containing the indicated UP element sequence. Asterisks (*) indicate promoters with single base pair mutations downstream of the transcription start site. The number of isolates obtained for each sequence is indicated in parentheses. Promoter activities are expressed relative to the activity of the "No UP" promoter (activity=1) and were determined from β-galactosidase measurements of λ lysogens containing promoter-lacZ fusions. Promoter activities differed by less than 4% in at least two experiments. C. Nucleotide frequencies (percentage of 8 sequences shown in FIG. 3B) for each proximal subsite position (−46 to −38).

Nineteen clones with the darkest red plaque color were analyzed by DNA sequencing, and eight different proximal subsite sequences were identified (FIGS. 3A–C). Six of the eight sequences contained a perfect A-tract from −46 to −41, and the remaining two contained near-perfect A-tracts (interrupted only by a T at position −42 or by a C at −46). There also was a bias for purines at positions −38 and −40. Promoter activities were quantified by measuring β-galactosidase activities of strains monolysogenic for phages containing the promoter-lacZ fusions. The proximal subsites stimulated transcription 82 to 170-fold (FIG. 3B), which is more than the stimulation observed with the wild type rrnB P1 UP element (SEQ ID NO:71) (69-fold), but less than the stimulation observed with the 4192 element (SEQ ID NO:40) (330-fold).

Identification of Optimal Distal Subsite Sequences

Based on plaque color, approximately 50% of the resulting selected promoters exhibited activities greater than that of the control promoter lacking an UP element, but none of these promoters were as active as wild type rrnB P1. From 21 clones producing the darkest red plaques, 19 different distal subsite sequences (i.e., distal accessory promoter elements) were identified (FIGS. 4B, C). The sequences had a high frequency of A residues at −57, A or T from −56 to −53, and T from −52 to −47 (FIG. 3C), and stimulated transcription 4- to 16-fold (FIG. 4B). This level of transcription stimulation is less than that observed with the 4192 element (SEQ ID NO:40), the proximal subsite (element 4549; SEQ ID NO:29), or even the rrnB P1 proximal subsite (SEQ ID NO:37).

Figures 5A, 5B:
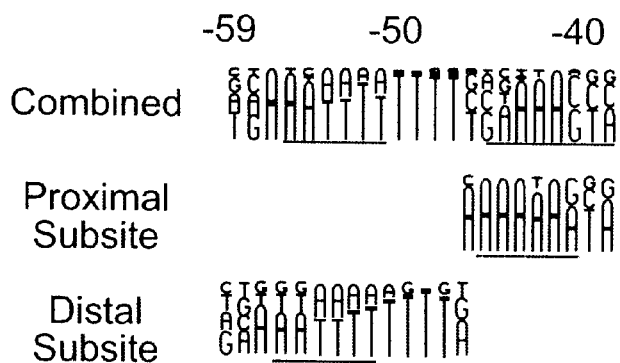
FIG. 5. Consensus sequences. A. Frequency diagrams of residues in the binding-selected combined UP elements and in the binding-selected proximal and distal subsites (from FIG. 3C and FIG. 4C). Each nucleotide is represented as a letter proportional in size to its frequency at that position in the selected population. The non-template strand positions protected by RNAP in hydroxyl radical footprints are indicated by horizontal lines under the protected bases. B. Consensus subsite sequences based on the nucleotide frequencies. One nucleotide is indicated when it is present in more than 70% of the population or two when together they represent 95% or more of the population. W=A or T; R=A or G; N=no single nucleotide present in 70% of the population and no two nucleotides make up 95% of the population.

Relationship between the Consensus Combined UP Element and the Consensus Subsite Sequences The distributions of nucleotides at each position in the selected proximal and distal subsite sequences are pictured in diagram form in FIG. 5A and compared with the distribution obtained in the combined UP element selection described in Example 1. FIG. 5B presents the derived consensus sequences.

The consensus proximal subsite sequence (i.e., the consensus proximal accessory promoter element) (SEQ ID NO:3) is related to the corresponding proximal region in the consensus combined UP element (SEQ ID NO:2). The consensus proximal subsite includes the three specified positions from the corresponding segment of the consensus combined UP element, −−41, −42, and −43, but it also contains five additional specified positions, with strong preference for A at −44, −45, and −46 and for purine at −25 38 and 40 (FIG. 5B).

In contrast, the consensus distal subsite sequence (i.e., the consensus distal accessory promoter element) (SEQ ID NO:4) is almost identical to that of the corresponding sequence from the wild type rrnB P1 (shown in FIG. 2) and consensus combined UP element (SEQ ID NO:2). Promoters were constructed containing the distal subsite from rrnB P1 (SEQ ID NO:25), or the distal subsite from the 4192 element and containing a non-functional proximal region. The resulting UP elements stimulated transcription in vivo 9- and 16-fold, respectively, consistent with their sequence similarity to the binding-selected distal subsites (rrnB P1 Distal and 4513; FIG. 4B).

The most active proximal and distal subsite sequences (4549 and 4513; FIGS. 3, 4), were combined to create the combined UP element 4541 (−59 to −38: 5'-GGAAAATTTTTTAAAAAAAGA (SEQ ID NO:1)). The stimulatory effect of the resulting combined UP element was 340-fold, which is very similar to the effect of the 4192 element.

In vitro transcription. In vitro transcription experiments were performed to establish that individual proximal and distal subsites, by themselves, stimulate transcription through interactions with αCTD. RNAPs containing different types of a subunits were used: wild type α; αΔ235 RNAP, which completely lacks the αCTD; and αR265A RNAP, which has a single amino acid substitution that disrupts αCTD-DNA interaction (Gaal, T. et al. (1996) *Genes Dev.* 10, 16–26; Murakami, K. et al. (1996) *EMBO J.* 15, 4358–4367).

Promoter fragments were cloned into pRLG770 (Ross, W. et al. (1990) *EMBO J.* 9, 3733–3742). Supercoiled DNA concentrations were determined both spectrophotometrically and by quantitation of the vector encoded RNA-1 transcripts under conditions of RNAP excess (40 nM). Transcription was carried out as previously described (Ross, W. et al. (1993) *Science* 262, 1407–13), except that reactions contained 0.6 nM DNA and 160 mM NaCl instead of KCl. The templates were supercoiled plasmids containing the rrnB P1 core promoter with the 4192 element, the 4547 proximal subsite, or the 4513 distal subsite. Transcriptional activities were quantified by phosphorimager analysis and calculated as a percentage of transcription with the wild type RNAP on the same template.

Reconstituted RNAPs (Gaal, T. et al. (1996) *Genes Dev.* 10, 16–26; Tang, H. et al. (1996) *Methods Enzymol* 273, 130–134) were used at concentrations that resulted in equivalent transcription from the lacUV5 promoter (2.7 nM for RNAP containing wild-type α, 9 nM for α R265A, 17.4 nM αΔ235).

The 4547 proximal and 4513 distal subsites increased transcription 10-fold and 9-fold, respectively. Under the same conditions, the 4192 element and the rrnB P1 UP element stimulated transcription by 47- and 21-fold, respectively. The individual subsites stimulate transcription and this stimulation requires no components other than promoter DNA and RNAP.

In in vitro transcription experiments with two mutant RNAP derivatives, αΔ235 RNAP and αR265A RNAP, the individual 4547 proximal and 4513 distal subsites, like rrnB P1 and the 4192 element, failed to stimulate transcription with αΔ235 RNAP and αR265A RNAP. This suggests that transcription stimulation by individual subsites requires αCTD-DNA interaction.

Hydroxyl radical footprinting. rrnB P1 promoter templates with different UP elements were generated by PCR from plasmids pRLG4213 (4547 proximal subsite), pRLG4214 (4513 distal subsite), pRLG3278 (4192 element), and pRLG4238 (−66 to +50 rrnB P1 promoter) using the vector-specific primers 5'-CCGCGGATCCGTATCACGAGGCCCTTTCG (SEQ ID NO:80) and 5'-GCGCTACGGCGTTTCAGTTC (SEQ ID NO:81). PCR conditions were as follows: 10 ng plasmid DNA, 2.5 units Taq polymerase, 10 mM Tris-Cl, pH 9.0, 50 mM KCl, 0.1% Triton X-100, 500 μM each dNTP, and 0.4 μg of each primer; 25 cycles of 95° C. for 1 minute, 45° C. for minute, 72° C. for 2 minutes. The PCR products were digested at a primer-encoded BamHI site (upstream of the EcoRI site), and end labeled with α[$^{32}$P]-dGTP (DuPont). Labeled fragments were purified, and hydroxyl radical footprint reactions were performed as described previously, except that in footprinting reactions with purified a the buffer contained 50 mM KCl and 9 mM NaCl. RNAP-bound complexes were isolated from 5% acrylamide gels following hydroxyl radical cleavage, eluted by diffusion, and purified using an Elutip (Schleicher and Schuell). Footprinting reactions were analyzed on 10% acrylamide-8M urea gels and quantified by phosphorimaging using ImageQuant software (Molecular Dynamics), normalized with Microsoft Excel, and plotted using SigmaPlot 4.0. Normalization of scans was done using a region outside of the protein binding site (−65 to −80) to correct for loading differences. Band intensities in different lanes were calculated as ratios of the lane with protein to that without protein.

When hydroxyl radical DNA footprinting experiments were performed using RNAP and promoters containing only the 4547 proximal subsite or only the 4513 distal subsite, strong protection (i.e., protection comparable to that in the −35 element region) was observed in the 4547 proximal subsite or the 4513 distal subsite subsite, and only weak protection was observed in the subsite that did not contain a nucleotide sequence corresponding to the consensus proximal or consensus distal subsite. When hydroxyl radical DNA footprinting experiments were performed using purified a and promoters containing only the 4547 proximal subsite or only the 4513 distal subsite, preferential protection was observed in the 4547 proximal subsite or the 4513 distal subsite subsite. This suggests that a single consensus subsite is sufficient for binding αCTD, both with RNAP and with purified α.

*E. coli* genome sequence analysis. Sequences of 253 confirmed mRNA promoters, 2,248 predicted mRNA promoters, 33 tRNA promoters, and 14 rRNA promoters from *E. coli* were obtained from Araceli Huerta and Julio Collado-Vides (http://www.cifn.unam.mx/Computational_Biology/*E.coli*-predictions/). Each promoter present in the database and used in the search was 31 nucleotides in length, including the proposed −35 hexamer and 25 nucleotides upstream of the −35 hexamer. Sequences were searched in GCG version 9.0 using the command FINDPATTERNS with the parameters −DAT=AAAAAARNR(N){7,7} −ONE −MIS=2 for the proximal subsite, −DAT=AWWWWWTTTTT(N){16,16} −ONE −MIS=2 for the distal subsite, and −DAT=AAAWWTWTTTTNAAASNN(N){7,7} −ONE −MIS=4 for the combined UP element.

The results of the search are presented in Table 2, which shows the statistics for *E. coli* mRNA, tRNA, or rRNA promoters having near-consensus subsites or combined UP elements (i.e., nucleotides −59 to −38). Table 3 provides the identities of these promoters. For the purposes of this discussion, near-consensus is defined as 0–2 differences from consensus per subsite or 0–4 differences from consensus per combined UP element.

TABLE 2

Near-consensus UP elements in *E. coli* promoters.

| | mRNA (2,501)[3] | tRNA (33)[3] | rRNA (14)[3] | total (2,548)[3] |
|---|---|---|---|---|
| consensus combined[1] | 10 (0.4%) | 3 (9.1%) | 3 (21%) | 16 (0.63%) |
| proximal subsite[2] | 76 (3.0%) | 8 (24%) | 5 (36%) | 89 (3.5%) |
| distal subsite[2] | 28 (1.1%) | 1 (3%) | 3 (21%) | 32 (1.3%) |

[1]Four or fewer mismatches to consensus.
[2]Two or fewer mismatches to consensus.
[3]The numbers in parentheses refer to the numbers of promoters searched from the *E. coli* promoter database (provided by A. Huerta and J. Collado-Vides). This database contains confirmed promoters and promoters predicted from sequence analysis (for sequences, see http://www.cifn.unam.mx/Computational_Biology/*E.coli*-predictions/).

TABLE 3

Promoters in *E. coli* genome with near consensus UP elements.[1]

| | combined UP elements (4 or fewer mismatches) | proximal subsites (2 or fewer mismatches) | distal subsites (2 or fewer mismatches) |
|---|---|---|---|
| mRNA | add, aslA, cspB, cspE, envR, hemL, | cspAp1, cspB, dinG, eco, fadL, gcvR, gidB, glnS, gut, | alpA, cirp2, envR, hdeD, hisL, |

TABLE 3-continued

Promoters in *E. coli* genome with near consensus UP elements.[1]

| | combined UP elements (4 or fewer mismatches) | proximal subsites (2 or fewer mismatches) | distal subsites (2 or fewer mismatches) |
|---|---|---|---|
| | hisL, ilvGMEDAp1, rpmFp1, 2118180 | hisL, hisS, hrpA, hupA, ilvGMEDAp2, lit, lpp, metG, polA, ppa, purH, recA, rob, srmB, sulA, syd, tdcR, thdF, tpiA, tpx, tsr, ugpp1, xylE, yadD, ybbB, ybeD, yehA, yfiD, yfig, ygfE, ygjE, ygjI, yhdW, yhiS, yibD, yidC, yjbA, yjgP, yjhD, yjiD, yjiT, yjjN, yohJ, 332725, 389475, 886646, 889312, 914128, 1168296, 1214698, 1431698, 1445540, 1627239, 1631646, 1732459, 1908123, 2183937, 2454832, 2680877, 2783031, 2890237, 2903664, 2983617, 3107570, 3170227, 3203897, 333657, 3578769 | ilvGMEDAp1, narU, ndk, phnA, ppsA, recN, rpmFp1, tsr, ycgB, yhaI, yhbY, yhiX, yifK, yjfZ, 240189, 535810, 675934, 851820, 1213282, 1215012, 1218824, 1906572, 2118180 |
| tRNA | argX, metT, valU | argX, asnU, aspV, glyW, metT, metZ, serT, serV | valU |
| rRNA | rrnAp1, rrnBp1, rrnCp1 | rrnAp2, rrnBp2, rrnCp2, rrnDp1, rrnGp1 | rrnAp1, rrnBp1, rrnCp1 |

[1]For predicted promoters of un-named genes, the numerical designations refer to the first position in the open reading frame. For actual promoter sequences, refer to http://www.cifn.unam.mx/Computational_Biology/*E.coli*-predictions/.

Several conclusions can be drawn from this analysis. First, numerous *E. coli* promoters contain single near-consensus subsites. Second, promoters with a single near-consensus subsite are significantly more common than promoters with a near-consensus combined UP element. Third, near-consensus proximal and distal subsites and combined UP elements occur significantly more frequently in stable RNA (rRNA and tRNA) promoters.

It is expected that compounds that functionally inactivate at least one αCTD, for instance small-molecule effectors, protein effectors, compounds that post-translationally modify an αCTD, or compounds that bind to UP elements and prevent the binding of αCTD to an UP element, may alter transcription of promoters that contain near-consensus or consensus proximal subsites, distal subsites, and combined UP elements.

Example 3

Identification of Compounds that Inhibit RNA Polymerase Binding to a Promoter

This example describes how an accessory promoter element can be used to screen for compounds that specifically inhibit transcription unit expression and potentially inhibit cell growth. The antibiotic used here is shown to interact with an accessory promoter element and specifically inhibit transcription in vitro.

The antibiotic distamyicn binds to A+T rich nucleotide sequences through interactions with the DNA minor groove (Coll et al. (1987) *Proc. Natl. Acad. Sci. USA* 84, 8385–8384). The α subunit of RNA polymerase and distamycin were incubated with a DNA fragment containing the rrnB P 1 core promoter and the proximal accessory promoter element 4547 (SEQ ID NO:32). Binding of the a subunit of RNA polymerase to the DNA in the presence of different distamycin concentrations was analyzed using electrophoretic mobility shift assays (FIG. 6A).

Electrophoretic mobility shift assays were performed as described in Gaal, T. et al. ((1996) *Genes Develop.* 10, 16–26). Briefly, reaction mixtures (20 μl) contained the $^{32}$P-3'-end labeled DNA fragment (about 0.01 to 0.1 nM and $10^7$ cpm/pmole), 20 mM Tris-HCl (pH 7.9), 20 mM NaCl, 1 mM EDTA, 10% glycerol, 5 μg/ml of sonicated salmon sperm DNA, and 0.15 nM to 1.5 μM of the a subunit. Reactions were incubated 15 minutes at 22° C., applied to 6% polyacrylamide, 10% glycerol slab gels in 0.5×TBE buffer, electrophoresed at 20 V/cm at 6° C. for 90 minutes, and the gels were dried and autoradiographed. Equilibrium constants were estimated from the concentration of a subunit required to shift 50% of the labeled fragment.

Half maximal inhibition of binding of the a subunit to the promoter fragment was achieved at a concentration of approximately 60 nM distamycin. Half maximal inhibition of transcription from the same promoter in plasmid RLG4213 was achieved at the same distamycin concentration (FIG. 6B) using the in vitro transcription assay under the conditions described in Examples 1 and 2. On the other hand, little or no transcription inhibition was observed at that distamycin concentration using the same promoter lacking the proximal accessory promoter element (i.e., containing SEQ ID NO:38 instead of SEQ ID NO:32) (FIG. 6B).

Hydroxy radical footprints were performed as described herein to determine whether distamycin preferentially bound to a proximal accessory promoter element. At a concentration of 125 nM, distamycin preferentially protected the proximal accessory promoter element and did not protect other regions of the fragment.

Thus, compounds that bind to an accessory promoter element can inhibit transcription. Novel compounds can be screened for inhibition of transcription from specific promoters that contain an accessory promoter element. Antibiotics with these properties could then be improved upon by chemical modification or alteration and screened for the ability to inhibit transcription in vitro and in vivo.

The complete disclosures of all patents, patent applications, publications, and nucleic acid and protein database entries, including for example GenBank accession numbers and EMBL accession numbers, that are cited herein are hereby incorporated by reference as if individually incorporated. Various modifications and alterations of this invention will become apparent to those skilled in the art without departing from the scope and spirit of this invention, and it should be understood that this invention is not to be unduly limited to the illustrative embodiments set forth herein.

| Sequence Listing Free Text | |
|---|---|
| SEQ ID NO:1 | combined accessory promoter element |
| SEQ ID NO:2 | Consensus combined accessory promoter element |
| SEQ ID NO:3 | Consensus proximal accessory promoter element |
| SEQ ID NO:4 | Consensus distal accessory promoter element |
| SEQ ID NO:5 | Nucleotide sequences at positions −59 to −38 upstream of a lac promoter |
| SEQ ID NOs:6–25 | Distal accessory promoter element |
| SEQ ID NO:26 | Distal subsite sequence with no accessory promoter element function |
| SEQ ID NO:27 | Distal accessory promoter element |
| SEQ ID NO:28 | Portion of promoter sequence used to identify distal accessory promoter elements |
| SEQ ID NOs:29–37 | Proximal accessory promoter element |
| SEQ ID NO:38 | Proximal subsite sequence with no accessory promoter element function |
| SEQ ID NO:39 | Portion of promoter sequence used to identify proximal accessory promoter elements |
| SEQ ID NOs:40–71 | combined accessory promoter element |
| SEQ ID NO:72 | Upstream sequence with no accessory promoter element function |
| SEQ ID NOs:73–89 | Oligonucleotide primer |

SEQUENCE LISTING

```
<160> NUMBER OF SEQ ID NOS: 89

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: combined
      accessory promoter element

<400> SEQUENCE: 1
ggaaaatttt tttaaaaaaa ga                                              22

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Consensus
      combined accessory promoter element
<221> NAME/KEY: misc_difference
<222> LOCATION: (1)..(2)
<223> OTHER INFORMATION: N = g, c, or t/u
<221> NAME/KEY: misc_difference
<222> LOCATION: (14)..(16)
<223> OTHER INFORMATION: N = a, g, c, or t/u
<221> NAME/KEY: misc_difference
<222> LOCATION: (20)..(22)
<223> OTHER INFORMATION: N = a, g, c, or t/u

<400> SEQUENCE: 2
nnaaawwtwt tttnnnaaan nn                                              22

<210> SEQ ID NO 3
<211> LENGTH: 9
<212> TYPE: DNA
<213> ORGANISM: Artificial Sequence
```

```
<220> FEATURE:
<223> OTHER INFORMATION: Description of Artificial Sequence: Consensus
      proximal accessory promoter element
<221> NAME/KEY: misc_difference
<222> LOCATION: (8)
<223> OTHER INFORMATION: N = a, g, c, or t/u

<400> SEQUENCE: 3 aaaaaarnr                                                                9

<210> SEQ ID NO 4
<211> LENGTH: 14
<212> TYPE: DNA
<213> ORGANISM: Artificial Sequence
<220> FEATURE:
<223> OTHER INFORMATION: Description of Artificial Sequence: Consensus
      distal accessory promoter element
<221> NAME/KEY: misc_difference
<222> LOCATION: (1)..(2)
<223> OTHER INFORMATION: N = a, g, c, or t/u
<221> NAME/KEY: misc_difference
<222> LOCATION: (14)
<223> OTHER INFORMATION: N = a, g, c, or t/u

<400> SEQUENCE: 4
nnawwwwwtt tttn                                                         14

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Nucleotide
      sequences at positions -59 to -38 upstream of a
      lac promoter

<400> SEQUENCE: 5
gactgcagtg gtacctagga gg                                                22

<210> SEQ ID NO 6
<211> LENGTH: 14
<212> TYPE: DNA
<213> ORGANISM: Artificial Sequence
<220> FEATURE:
<223> OTHER INFORMATION: Description of Artificial Sequence: Distal
      accessory promoter element

<400> SEQUENCE: 6
agaaaaatat tttg                                                         14

<210> SEQ ID NO 7
<211> LENGTH: 14
<212> TYPE: DNA
<213> ORGANISM: Artificial Sequence
<220> FEATURE:
<223> OTHER INFORMATION: Description of Artificial Sequence: Distal
      accessory promoter element

<400> SEQUENCE: 7 gcatttttt ttca                                                          14

<210> SEQ ID NO 8
<211> LENGTH: 14
<212> TYPE: DNA
<213> ORGANISM: Artificial Sequence
<220> FEATURE:
<223> OTHER INFORMATION: Description of Artificial Sequence: Distal
      accessory promoter element
```

```
<400> SEQUENCE: 8
gtaaaaattt ttta                                                    14

<210> SEQ ID NO 9
<211> LENGTH: 14
<212> TYPE: DNA
<213> ORGANISM: Artificial Sequence
<220> FEATURE:
<223> OTHER INFORMATION: Description of Artificial Sequence: Distal
      accessory promoter element

<400> SEQUENCE: 9
acgtattttt ttta                                                    14

<210> SEQ ID NO 10
<211> LENGTH: 14
<212> TYPE: DNA
<213> ORGANISM: Artificial Sequence
<220> FEATURE:
<223> OTHER INFORMATION: Description of Artificial Sequence: Distal
      accessory promoter element

<400> SEQUENCE: 10
gaaaaatatt tttg                                                    14

<210> SEQ ID NO 11
<211> LENGTH: 14
<212> TYPE: DNA
<213> ORGANISM: Artificial Sequence
<220> FEATURE:
<223> OTHER INFORMATION: Description of Artificial Sequence: Distal
      accessory promoter element

<400> SEQUENCE: 11
taaaaaatat ttta                                                    14

<210> SEQ ID NO 12
<211> LENGTH: 14
<212> TYPE: DNA
<213> ORGANISM: Artificial Sequence
<220> FEATURE:
<223> OTHER INFORMATION: Description of Artificial Sequence: Distal
      accessory promoter element

<400> SEQUENCE: 12
taagtttttt ttta                                                    14

<210> SEQ ID NO 13
<211> LENGTH: 14
<212> TYPE: DNA
<213> ORGANISM: Artificial Sequence
<220> FEATURE:
<223> OTHER INFORMATION: Description of Artificial Sequence: Distal
      accessory promoter element

<400> SEQUENCE: 13
aaaaatttat tttg                                                    14

<210> SEQ ID NO 14
<211> LENGTH: 14
<212> TYPE: DNA
<213> ORGANISM: Artificial Sequence
<220> FEATURE:
<223> OTHER INFORMATION: Description of Artificial Sequence: Distal
      accessory promoter element

<400> SEQUENCE: 14
```
cgaaaaaaaa ttta                                                  14

<210> SEQ ID NO 15
<211> LENGTH: 14
<212> TYPE: DNA
<213> ORGANISM: Artificial Sequence
<220> FEATURE:
<223> OTHER INFORMATION: Description of Artificial Sequence: Distal
      accessory promoter element

<400> SEQUENCE: 15
ccggtttttt ttta                                                  14

<210> SEQ ID NO 16
<211> LENGTH: 14
<212> TYPE: DNA
<213> ORGANISM: Artificial Sequence
<220> FEATURE:
<223> OTHER INFORMATION: Description of Artificial Sequence: Distal
      accessory promoter element

<400> SEQUENCE: 16
taaatttttt tttt                                                  14

<210> SEQ ID NO 17
<211> LENGTH: 14
<212> TYPE: DNA
<213> ORGANISM: Artificial Sequence
<220> FEATURE:
<223> OTHER INFORMATION: Description of Artificial Sequence: Distal
      accessory promoter element

<400> SEQUENCE: 17
gaaaaaaata gttg                                                  14

<210> SEQ ID NO 18
<211> LENGTH: 14
<212> TYPE: DNA
<213> ORGANISM: Artificial Sequence
<220> FEATURE:
<223> OTHER INFORMATION: Description of Artificial Sequence: Distal
      accessory promoter element

<400> SEQUENCE: 18
atatgttttt ttta                                                  14

<210> SEQ ID NO 19
<211> LENGTH: 14
<212> TYPE: DNA
<213> ORGANISM: Artificial Sequence
<220> FEATURE:
<223> OTHER INFORMATION: Description of Artificial Sequence: Distal
      accessory promoter element

<400> SEQUENCE: 19
agatttattt ttct                                                  14

<210> SEQ ID NO 20
<211> LENGTH: 14
<212> TYPE: DNA
<213> ORGANISM: Artificial Sequence
<220> FEATURE:
<223> OTHER INFORMATION: Description of Artificial Sequence: Distal
      accessory promoter element

<400> SEQUENCE: 20

```
gataaaaata gttg                                              14
```

<210> SEQ ID NO 21
<211> LENGTH: 14
<212> TYPE: DNA
<213> ORGANISM: Artificial Sequence
<220> FEATURE:
<223> OTHER INFORMATION: Description of Artificial Sequence: Distal
      accessory promoter element

<400> SEQUENCE: 21

```
gtatgatttt ttta                                              14
```

<210> SEQ ID NO 22
<211> LENGTH: 14
<212> TYPE: DNA
<213> ORGANISM: Artificial Sequence
<220> FEATURE:
<223> OTHER INFORMATION: Description of Artificial Sequence: Distal
      accessory promoter element

<400> SEQUENCE: 22

```
ataaaatatt ttat                                              14
```

<210> SEQ ID NO 23
<211> LENGTH: 14
<212> TYPE: DNA
<213> ORGANISM: Artificial Sequence
<220> FEATURE:
<223> OTHER INFORMATION: Description of Artificial Sequence: Distal
      accessory promoter element

<400> SEQUENCE: 23

```
gcaaatatat tttt                                              14
```

<210> SEQ ID NO 24
<211> LENGTH: 14
<212> TYPE: DNA
<213> ORGANISM: Artificial Sequence
<220> FEATURE:
<223> OTHER INFORMATION: Description of Artificial Sequence: Distal
      accessory promoter element

<400> SEQUENCE: 24

```
tgtaataatt ttta                                              14
```

<210> SEQ ID NO 25
<211> LENGTH: 14
<212> TYPE: DNA
<213> ORGANISM: Artificial Sequence
<220> FEATURE:
<223> OTHER INFORMATION: Description of Artificial Sequence: Distal
      accessory promoter element

<400> SEQUENCE: 25

```
agaaaattat ttta                                              14
```

<210> SEQ ID NO 26
<211> LENGTH: 14
<212> TYPE: DNA
<213> ORGANISM: Artificial Sequence
<220> FEATURE:
<223> OTHER INFORMATION: Description of Artificial Sequence: Distal
      subsite sequence with no accessory promoter element function

<400> SEQUENCE: 26

```
gactgcagtg gtac                                              14
```

```
<210> SEQ ID NO 27
<211> LENGTH: 14
<212> TYPE: DNA
<213> ORGANISM: Artificial Sequence
<220> FEATURE:
<223> OTHER INFORMATION: Description of Artificial Sequence: Distal
      accessory promoter element

<400> SEQUENCE: 27
ggaaaatttt tttt                                                        14

<210> SEQ ID NO 28
<211> LENGTH: 29
<212> TYPE: DNA
<213> ORGANISM: Artificial Sequence
<220> FEATURE:
<223> OTHER INFORMATION: Description of Artificial Sequence:  Portion of
      promoter sequence used to identify distal
      accessory promoter elements
<221> NAME/KEY: misc_difference
<222> LOCATION: (1)..(14)
<223> OTHER INFORMATION: N = a, g, c, or t/u

<400> SEQUENCE: 28
nnnnnnnnnn nnnnctagga atcttgtca                                        29

<210> SEQ ID NO 29
<211> LENGTH: 9
<212> TYPE: DNA
<213> ORGANISM: Artificial Sequence
<220> FEATURE:
<223> OTHER INFORMATION: Description of Artificial Sequence: Proximal
      accessory promoter element

<400> SEQUENCE: 29 aaaaaaaga                                                               9

<210> SEQ ID NO 30
<211> LENGTH: 9
<212> TYPE: DNA
<213> ORGANISM: Artificial Sequence
<220> FEATURE:
<223> OTHER INFORMATION: Description of Artificial Sequence: Proximal
      accessory promoter element

<400> SEQUENCE: 30 aaaaaaaca                                                               9

<210> SEQ ID NO 31
<211> LENGTH: 9
<212> TYPE: DNA
<213> ORGANISM: Artificial Sequence
<220> FEATURE:
<223> OTHER INFORMATION: Description of Artificial Sequence: Proximal
      accessory promoter element

<400> SEQUENCE: 31 aaaaaaatg                                                               9

<210> SEQ ID NO 32
<211> LENGTH: 9
<212> TYPE: DNA
<213> ORGANISM: Artificial Sequence
<220> FEATURE:
<223> OTHER INFORMATION: Description of Artificial Sequence: Proximal
      accessory promoter element
```

-continued

```
<400> SEQUENCE: 32 aaaaaagta                                                                9

<210> SEQ ID NO 33
<211> LENGTH: 9
<212> TYPE: DNA
<213> ORGANISM: Artificial Sequence
<220> FEATURE:
<223> OTHER INFORMATION: Description of Artificial Sequence: Proximal
      accessory promoter element

<400> SEQUENCE: 33 aaaaaagtg                                                                9

<210> SEQ ID NO 34
<211> LENGTH: 9
<212> TYPE: DNA
<213> ORGANISM: Artificial Sequence
<220> FEATURE:
<223> OTHER INFORMATION: Description of Artificial Sequence: Proximal
      accessory promoter element

<400> SEQUENCE: 34 aaaatagta                                                                9

<210> SEQ ID NO 35
<211> LENGTH: 9
<212> TYPE: DNA
<213> ORGANISM: Artificial Sequence
<220> FEATURE:
<223> OTHER INFORMATION: Description of Artificial Sequence: Proximal
      accessory promoter element

<400> SEQUENCE: 35 caaaaaaca                                                                9

<210> SEQ ID NO 36
<211> LENGTH: 9
<212> TYPE: DNA
<213> ORGANISM: Artificial Sequence
<220> FEATURE:
<223> OTHER INFORMATION: Description of Artificial Sequence: Proximal
      accessory promoter element

<400> SEQUENCE: 36 aaaaaaata                                                                9

<210> SEQ ID NO 37
<211> LENGTH: 9
<212> TYPE: DNA
<213> ORGANISM: Artificial Sequence
<220> FEATURE:
<223> OTHER INFORMATION: Description of Artificial Sequence: Proximal
      accessory promoter element

<400> SEQUENCE: 37 aaatttcct                                                                9

<210> SEQ ID NO 38
<211> LENGTH: 9
<212> TYPE: DNA
<213> ORGANISM: Artificial Sequence
<220> FEATURE:
<223> OTHER INFORMATION: Description of Artificial Sequence: Proximal
      subsite sequence with no accessory promoter
      element function
```

```
<400> SEQUENCE: 38 cctaggaat                                                                9

<210> SEQ ID NO 39
<211> LENGTH: 29
<212> TYPE: DNA
<213> ORGANISM: Artificial Sequence
<220> FEATURE:
<223> OTHER INFORMATION: Description of Artificial Sequence: Portion of
      promoter sequence used to identify proximal
      accessory promoter elements
<221> NAME/KEY: misc_difference
<222> LOCATION: (14)..(22)
<223> OTHER INFORMATION: N = a, g, c, or t/u

<400> SEQUENCE: 39
gactgcagtg gtannnnnnn nncttgtca                                         29

<210> SEQ ID NO 40
<211> LENGTH: 22
<212> TYPE: DNA
<213> ORGANISM: Artificial Sequence
<220> FEATURE:
<223> OTHER INFORMATION: Description of Artificial Sequence: combined
      accessory promoter element

<400> SEQUENCE: 40
ggaaaatttt ttttcaaaag ta                                                22

<210> SEQ ID NO 41
<211> LENGTH: 22
<212> TYPE: DNA
<213> ORGANISM: Artificial Sequence
<220> FEATURE:
<223> OTHER INFORMATION: Description of Artificial Sequence: combined
      accessory promoter element

<400> SEQUENCE: 41 agaaatttt tttcgaaaaa ca                                                 22

<210> SEQ ID NO 42
<211> LENGTH: 22
<212> TYPE: DNA
<213> ORGANISM: Artificial Sequence
<220> FEATURE:
<223> OTHER INFORMATION: Description of Artificial Sequence: combined
      accessory promoter element

<400> SEQUENCE: 42
taaaaatttt ttttgaaaag gg                                                22

<210> SEQ ID NO 43
<211> LENGTH: 22
<212> TYPE: DNA
<213> ORGANISM: Artificial Sequence
<220> FEATURE:
<223> OTHER INFORMATION: Description of Artificial Sequence: combined
      accessory promoter element

<400> SEQUENCE: 43
caaaaatatt tttgaaaaaa ga                                                22

<210> SEQ ID NO 44
<211> LENGTH: 22
<212> TYPE: DNA
<213> ORGANISM: Artificial Sequence
<220> FEATURE:
```

```
<223> OTHER INFORMATION: Description of Artificial Sequence: combined
      accessory promoter element

<400> SEQUENCE: 44
ggaaatattt tttcataaac cc                                              22

<210> SEQ ID NO 45
<211> LENGTH: 22
<212> TYPE: DNA
<213> ORGANISM: Artificial Sequence
<220> FEATURE:
<223> OTHER INFORMATION: Description of Artificial Sequence: combined
      accessory promoter element

<400> SEQUENCE: 45
agaaaaatat tttcgaaaac ta                                              22

<210> SEQ ID NO 46
<211> LENGTH: 22
<212> TYPE: DNA
<213> ORGANISM: Artificial Sequence
<220> FEATURE:
<223> OTHER INFORMATION: Description of Artificial Sequence: combined
      accessory promoter element

<400> SEQUENCE: 46
aaaaatattt tttcgaaaag ta                                              22

<210> SEQ ID NO 47
<211> LENGTH: 22
<212> TYPE: DNA
<213> ORGANISM: Artificial Sequence
<220> FEATURE:
<223> OTHER INFORMATION: Description of Artificial Sequence: combined
      accessory promoter element

<400> SEQUENCE: 47
taaatttttt tttgcaaaag ta                                              22

<210> SEQ ID NO 48
<211> LENGTH: 22
<212> TYPE: DNA
<213> ORGANISM: Artificial Sequence
<220> FEATURE:
<223> OTHER INFORMATION: Description of Artificial Sequence: combined
      accessory promoter element

<400> SEQUENCE: 48
acaaaaatat ttttcaaaac cc                                              22

<210> SEQ ID NO 49
<211> LENGTH: 22
<212> TYPE: DNA
<213> ORGANISM: Artificial Sequence
<220> FEATURE:
<223> OTHER INFORMATION: Description of Artificial Sequence: combined
      accessory promoter element

<400> SEQUENCE: 49
ttaaattttt tttcgtaaac cc                                              22

<210> SEQ ID NO 50
<211> LENGTH: 22
<212> TYPE: DNA
<213> ORGANISM: Artificial Sequence
<220> FEATURE:
<223> OTHER INFORMATION: Description of Artificial Sequence: combined
``` accessory promoter element

<400> SEQUENCE: 50
ttaaattttt tttcataaac cc                                              22

<210> SEQ ID NO 51
<211> LENGTH: 22
<212> TYPE: DNA
<213> ORGANISM: Artificial Sequence
<220> FEATURE:
<223> OTHER INFORMATION: Description of Artificial Sequence: combined
      accessory promoter element

<400> SEQUENCE: 51
tcaaattttt ttttgcaaac cc                                              22

<210> SEQ ID NO 52
<211> LENGTH: 22
<212> TYPE: DNA
<213> ORGANISM: Artificial Sequence
<220> FEATURE:
<223> OTHER INFORMATION: Description of Artificial Sequence: combined
      accessory promoter element

<400> SEQUENCE: 52
caaatttttt tttgctaaac cc                                              22

<210> SEQ ID NO 53
<211> LENGTH: 22
<212> TYPE: DNA
<213> ORGANISM: Artificial Sequence
<220> FEATURE:
<223> OTHER INFORMATION: Description of Artificial Sequence: combined
      accessory promoter element

<400> SEQUENCE: 53
aaaaatattt ttttgaaaag ta                                              22

<210> SEQ ID NO 54
<211> LENGTH: 22
<212> TYPE: DNA
<213> ORGANISM: Artificial Sequence
<220> FEATURE:
<223> OTHER INFORMATION: Description of Artificial Sequence: combined
      accessory promoter element

<400> SEQUENCE: 54
taaaaatatt tttcgtttac cc                                              22

<210> SEQ ID NO 55
<211> LENGTH: 22
<212> TYPE: DNA
<213> ORGANISM: Artificial Sequence
<220> FEATURE:
<223> OTHER INFORMATION: Description of Artificial Sequence: combined
      accessory promoter element

<400> SEQUENCE: 55
acaaaaatat ttttcgaaac cc                                              22

<210> SEQ ID NO 56
<211> LENGTH: 22
<212> TYPE: DNA
<213> ORGANISM: Artificial Sequence
<220> FEATURE:
<223> OTHER INFORMATION: Description of Artificial Sequence: combined
      accessory promoter element

```
<400> SEQUENCE: 56
tcaaaatttt ttttgcaaag ta                                              22

<210> SEQ ID NO 57
<211> LENGTH: 22
<212> TYPE: DNA
<213> ORGANISM: Artificial Sequence
<220> FEATURE:
<223> OTHER INFORMATION: Description of Artificial Sequence: combined
      accessory promoter element

<400> SEQUENCE: 57
tgaatttttt tttcgtctac cc                                              22

<210> SEQ ID NO 58
<211> LENGTH: 22
<212> TYPE: DNA
<213> ORGANISM: Artificial Sequence
<220> FEATURE:
<223> OTHER INFORMATION: Description of Artificial Sequence: combined
      accessory promoter element

<400> SEQUENCE: 58
agaaaaatat ttttgaaaac ta                                              22

<210> SEQ ID NO 59
<211> LENGTH: 22
<212> TYPE: DNA
<213> ORGANISM: Artificial Sequence
<220> FEATURE:
<223> OTHER INFORMATION: Description of Artificial Sequence: combined
      accessory promoter element

<400> SEQUENCE: 59
gcaaaataat tgtaaaaaag ta                                              22

<210> SEQ ID NO 60
<211> LENGTH: 22
<212> TYPE: DNA
<213> ORGANISM: Artificial Sequence
<220> FEATURE:
<223> OTHER INFORMATION: Description of Artificial Sequence: combined
      accessory promoter element

<400> SEQUENCE: 60
agaaatttat tttaaaaaag gg                                              22

<210> SEQ ID NO 61
<211> LENGTH: 22
<212> TYPE: DNA
<213> ORGANISM: Artificial Sequence
<220> FEATURE:
<223> OTHER INFORMATION: Description of Artificial Sequence: combined
      accessory promoter element

<400> SEQUENCE: 61
tgaaaaatat ttttgaaaac ta                                              22

<210> SEQ ID NO 62
<211> LENGTH: 22
<212> TYPE: DNA
<213> ORGANISM: Artificial Sequence
<220> FEATURE:
<223> OTHER INFORMATION: Description of Artificial Sequence: combined
      accessory promoter element
```

-continued

```
<400> SEQUENCE: 62
taaactattt tttcaaaaag ga                                              22

<210> SEQ ID NO 63
<211> LENGTH: 22
<212> TYPE: DNA
<213> ORGANISM: Artificial Sequence
<220> FEATURE:
<223> OTHER INFORMATION: Description of Artificial Sequence: combined
      accessory promoter element

<400> SEQUENCE: 63
tgaaatttat tttgcgaaag gg                                              22

<210> SEQ ID NO 64
<211> LENGTH: 22
<212> TYPE: DNA
<213> ORGANISM: Artificial Sequence
<220> FEATURE:
<223> OTHER INFORMATION: Description of Artificial Sequence: combined
      accessory promoter element

<400> SEQUENCE: 64
taaacttttt ttttcgaaag tg                                              22

<210> SEQ ID NO 65
<211> LENGTH: 22
<212> TYPE: DNA
<213> ORGANISM: Artificial Sequence
<220> FEATURE:
<223> OTHER INFORMATION: Description of Artificial Sequence: combined
      accessory promoter element

<400> SEQUENCE: 65
tgaaatattt ttttgaaaac cc                                              22

<210> SEQ ID NO 66
<211> LENGTH: 22
<212> TYPE: DNA
<213> ORGANISM: Artificial Sequence
<220> FEATURE:
<223> OTHER INFORMATION: Description of Artificial Sequence: combined
      accessory promoter element

<400> SEQUENCE: 66
agattttttt tttgtaaaag tg                                              22

<210> SEQ ID NO 67
<211> LENGTH: 22
<212> TYPE: DNA
<213> ORGANISM: Artificial Sequence
<220> FEATURE:
<223> OTHER INFORMATION: Description of Artificial Sequence: combined
      accessory promoter element

<400> SEQUENCE: 67
gcaaaaatat ttcgtcaaac cc                                              22

<210> SEQ ID NO 68
<211> LENGTH: 22
<212> TYPE: DNA
<213> ORGANISM: Artificial Sequence
<220> FEATURE:
<223> OTHER INFORMATION: Description of Artificial Sequence: combined
      accessory promoter element

<400> SEQUENCE: 68
```

```
gaaaaatatt tttgataaag ta                                              22

<210> SEQ ID NO 69
<211> LENGTH: 22
<212> TYPE: DNA
<213> ORGANISM: Artificial Sequence
<220> FEATURE:
<223> OTHER INFORMATION: Description of Artificial Sequence: combined
      accessory promoter element

<400> SEQUENCE: 69
gcaaaattat tttgctaaag ta                                              22

<210> SEQ ID NO 70
<211> LENGTH: 22
<212> TYPE: DNA
<213> ORGANISM: Artificial Sequence
<220> FEATURE:
<223> OTHER INFORMATION: Description of Artificial Sequence: combined
      accessory promoter element

<400> SEQUENCE: 70
gaaaatatat ttttcaaaag ta                                              22

<210> SEQ ID NO 71
<211> LENGTH: 22
<212> TYPE: DNA
<213> ORGANISM: Artificial Sequence
<220> FEATURE:
<223> OTHER INFORMATION: Description of Artificial Sequence: combined
      accessory promoter element

<400> SEQUENCE: 71
agaaaattat tttaaatttc ct                                              22

<210> SEQ ID NO 72
<211> LENGTH: 22
<212> TYPE: DNA
<213> ORGANISM: Artificial Sequence
<220> FEATURE:
<223> OTHER INFORMATION: Description of Artificial Sequence:  Upstream
      sequence with no accessory promoter element
      function

<400> SEQUENCE: 72
gactgcagtg gtacctagga at                                              22

<210> SEQ ID NO 73
<211> LENGTH: 67
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 73
cgcggtcgac tgcagtggta cctaggaatc ttgtcaggcc ggaataactc cctataatgc     60
gccacca                                                               67

<210> SEQ ID NO 74
<211> LENGTH: 67
<212> TYPE: DNA
<213> ORGANISM: Artificial Sequence
<220> FEATURE:
<223> OTHER INFORMATION: Description of Artificial Sequence:
      Oligonucleotide primer
```

<400> SEQUENCE: 74
cgcggtcaga aaattatttt aaatttcctc ttgtcaggcc ggaataactc cctataatgc    60
gccacca                                                             67

<210> SEQ ID NO 75
<211> LENGTH: 29
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 75
ccgcggatcc gtatcacgag gcccttcg                                      29

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 76
gcgctacggc gtttcagttc                                               20

<210> SEQ ID NO 77
<211> LENGTH: 34
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 77
gacgtcagga attccgcggt cgactgcagt ggta                               34

<210> SEQ ID NO 78
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 78
gacgtcagga attccgcggt c                                             21

<210> SEQ ID NO 79
<211> LENGTH: 109
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 79
gtccaagctt ggtcaggaga accccgctga cccggcggcg tgtttgccgt tgttccgtgt    60
cagtggtggc gcattatagg gagttattcc ggcctgacaa gattcctag              109

<210> SEQ ID NO 80
<211> LENGTH: 29
<212> TYPE: DNA
<213> ORGANISM: Artificial Sequence

```
<220> FEATURE:
<223> OTHER INFORMATION: Description of Artificial Sequence:
      Oligonucleotide primer

<400> SEQUENCE: 80
ccgcggatcc gtatcacgag gcccttttcg                                              29

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 81
gcgctacggc gtttcagttc                                                         20

<210> SEQ ID NO 82
<211> LENGTH: 80
<212> TYPE: DNA
<213> ORGANISM: Artificial Sequence
<220> FEATURE:
<223> OTHER INFORMATION: Description of Artificial Sequence:
      Oligonucleotide primer
<221> NAME/KEY: misc_difference
<222> LOCATION: (22)..(43)
<223> OTHER INFORMATION: N = a, g, c, or t/u

<400> SEQUENCE: 82
gacgtcagga attccgcggt cnnnnnnnnn nnnnnnnnnn nnncttgtca ggccggaata            60
actccctata atgcgccacc                                                        80

<210> SEQ ID NO 83
<211> LENGTH: 81
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 83
gtcgaagctt ggtcaggaga accccgctga cccggcggcg tgtttgccgt tgttccgtgt            60
cagtggtggc gcattatagg g                                                      81

<210> SEQ ID NO 84
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 84
aggctttaca ctttatgctt ccggctcgta tgttgtgtgg                                  40

<210> SEQ ID NO 85
<211> LENGTH: 64
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 85
gaattctcac tcattaggca ccccaggctt tacactttat gcttccggct cgtataatgt            60
```

```
gtgg                                                                64
```

```
<210> SEQ ID NO 86
<211> LENGTH: 80
<212> TYPE: DNA
<213> ORGANISM: Artificial Sequence
<220> FEATURE:
<223> OTHER INFORMATION: Description of Artificial Sequence:
      Oligonucleotide primer
<221> NAME/KEY: misc_difference
<222> LOCATION: (35)..(43)
<223> OTHER INFORMATION: N = a, g, c, or t/u

<400> SEQUENCE: 86
gacctcagga attccgcggt cgactgcagt ggtannnnnn nnncttgtca ggccggaata     60
actccctata atgcgccacc                                                80
```

```
<210> SEQ ID NO 87
<211> LENGTH: 80
<212> TYPE: DNA
<213> ORGANISM: Artificial Sequence
<220> FEATURE:
<223> OTHER INFORMATION: Description of Artificial Sequence:
      Oligonucleotide primer
<221> NAME/KEY: misc_difference
<222> LOCATION: (22)..(35)
<223> OTHER INFORMATION: N = a, g, c, or t/u

<400> SEQUENCE: 87
gacgtcagga attccgcggt cnnnnnnnnn nnnnnctagg aatcttgtca ggccggaata     60
actccctata atgcgccacc                                                80
```

```
<210> SEQ ID NO 88
<211> LENGTH: 101
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 88
gtccaagctt ggtcaggaga accccgctga cccggcggcg tgtttgccgt tgttccgtgt     60
cagtggtggc gcattatagg gagttattcc ggcctgacaa g                        101
```

```
<210> SEQ ID NO 89
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 89
gacgtcagga attccgcgg                                                 19
```

What is claimed is:

1. A method for detecting whether a compound alters transcription of a transcription unit, the method comprising:

providing in a reaction mixture a first polynucleotide comprising a first promoter operably linked to a transcription unit, wherein the first promoter comprises an accessory promoter element and a core promoter element, wherein the accessory promoter element is selected from the group consisting of a distal accessory promoter element, a proximal accessory promoter element, and a combined accessory promoter element, and wherein the reaction mixture comprises at least one RNA polymerase;

adding an amount of the compound to be tested to the reaction mixture under conditions effective to cause transcription;

detecting an amount of a transcription product; and comparing the amount of the transcription product in the presence of the compound to an amount of the transcription product in the absence of the compound under the same conditions, wherein the compound does not alter the amount of a transcription product from a second polynucleotide, the second polynucleotide comprising a second promoter operably linked to the same transcription unit that is operably linked to the first promoter, the second promoter consisting of the same core promoter element of the first promoter.

2. The method of claim 1 wherein transcription of the transcription unit is decreased.

3. The method of claim 1 wherein the reaction mixture comprises an rNTP comprising a detectable label.

4. The method of claim 3 wherein the detectable label is selected from the group consisting of a radioactive label, a fluorescent label, an enzymatic label, and a combination thereof.

5. The method of claim 1 wherein the transcription unit further comprises a coding region.

6. The method of claim 1 wherein the coding region encodes a detectable marker.

7. The method of claim 6 wherein the detectable marker is selected from the group consisting of β-galactosidase, green fluorescent protein, luciferase, and chloramphenicol acetyl transferase.

8. The method of claim 5 wherein the reaction mixture further comprises a detectably labeled amino acid.

9. The method of claim 8 wherein the detectable label is selected from the group consisting of a radioactive label, a fluorescent label, an enzymatic label, and a combination thereof.

10. The method of claim 1 wherein the proximal accessory promoter element comprises a nucleotide sequence selected from the group consisting of SEQ ID NOs: 29–33 and complements thereof.

11. The method of claim 1 wherein the combined accessory promoter element comprises a nucleotide sequence selected from the group consisting of SEQ ID NOs:40–44 and complements thereof.

12. The method of claim 1 wherein the polynucleotide is present on a plasmid vector.

* * * * *

UNITED STATES PATENT AND TRADEMARK OFFICE
CERTIFICATE OF CORRECTION

PATENT NO.      : 6,605,431 B1
DATED           : August 12, 2003
INVENTOR(S)     : Gourse et al.

It is certified that error appears in the above-identified patent and that said Letters Patent is hereby corrected as shown below:

Title page,
Item [56], References Cited, OTHER PUBLICATIONS, insert
-- Title Pages, Chapters 1-5, Appendices A-D of dissertation by Shawn T. Estrem, entitled, "The Identification of an UP Element Consensus and Characterization of Its Interactions with the $\alpha$ Subunit and RNA Polymerase, " 1999, University of Wisconsin-Madison. --;
"S.E. Aiyar et al (1998)", reference, delete "Polymerase Subunit" and insert
-- Polymerase $\alpha$ Subunit --;
"E.E. Blatter et al. (1994)", reference, delete "Polymerase Subunit" and insert
-- Polymerase $\alpha$ Subunit: --;
"S.T. Estrem et al. (1999)", reference, delete "Polymerase Subunit," and insert
-- Polymerase $\alpha$ Subunit, --;
"T. Gaal et al. (1996)", reference, delete "Determinants of the Subunit" and insert
-- Determinants of the $\alpha$ Subunit --;
"K. Murakami et al. (1996)", reference, delete "Polymerase Subunit," and insert
-- Polymerase $\alpha$ Subunit, --;
"W. Ross et al. (1993)", reference, delete "Binding by the Subunit," and insert
-- Binding by the $\alpha$ Subunit, --

Column 1,
Line 37, delete "by the a" and insert -- by the $\sigma$ --
Line 63, delete "by a remain" and insert -- by $\alpha$ remain --
Line 65, delete "different a" and insert -- different $\sigma$ --

Column 3,
Line 44, delete "thereof Optionally," and insert -- thereof. Optionally, --

Column 5,
Line 34, delete "strain RLG3Q97)" and insert -- strain RLG3097) --

Column 7,
Line 16, delete "accessory. promoter" and insert -- accessory promoter --
Line 27, delete "thymidine, Preferably" and insert -- thymidine. Preferably --

Column 11,
Line 49, delete "preferably 20 about" and insert -- preferably about --

Column 12,
Line 47, delete "the a subunit" and insert -- the $\alpha$ subunit --

UNITED STATES PATENT AND TRADEMARK OFFICE
CERTIFICATE OF CORRECTION

PATENT NO.    : 6,605,431 B1
DATED         : August 12, 2003
INVENTOR(S)   : Gourse et al.

It is certified that error appears in the above-identified patent and that said Letters Patent is hereby corrected as shown below:

Column 15,
Line 13, delete "with the a subunit" and insert -- with the α subunit --
Lines 28-29, delete "purified a subunit" and insert -- purified α subunit --
Line 34, delete "function Lisser," and insert -- function (Lisser, --
Line 39, delete "in the -first" and insert -- in the first --

Column 16,
Line 17, delete "C. in" and insert -- C in --
Line 21, delete "46344638." and insert -- 4634-4638. --

Column 18,
Line 37, delete "466475;" and insert -- 466-475; --
Line 43, delete "92 3733-3742)." and insert -- 9,3733-3742). --
Line 49, delete "RNAP a subunit." and insert -- RNAP α subunit. --

Column 19,
Line 7, delete "sequences n vivo." and insert -- sequences *in vivo.* --
Line 35, delete "C. for 4" and insert -- C for 4 --
Line 37, delete "C. for 30" and insert -- C for 30 --
Line 42, delete "C. with 59" and insert -- C with 59 --
Line 49, delete "or purified a" and insert -- or purified α --
Line 51, delete "C. with 16" and insert -- C with 16 --
Line 54, delete "and the a subunit" and insert -- and the α subunit --

Column 21,
Lines 17-18, delete "95° C. for 5 minutes, 53.5° C. for 1 minute, 72° C. for" and insert -- 95° C for 5 minutes, 53.5° C for 1 minute, 72° C. for --

Column 22,
Line 21, delete "element, - -41," and insert -- element, -41 --
Lines 23-24, delete "at -25 38 and 40" and insert -- at -38 and -40 --
Line 48, delete "types of a subunits" and insert -- types of α subunits --

Column 23,
Lines 32-33, delete "95° C. for 1 minute, 45° C. for minute, 72° C. for 2" and insert -- 95° C for 1 minute, 45° C for 1 minute, 72° C for 2 --
Line 38, delete "purified a the" and insert -- purified α the --

UNITED STATES PATENT AND TRADEMARK OFFICE
CERTIFICATE OF CORRECTION

PATENT NO. : 6,605,431 B1
DATED : August 12, 2003
INVENTOR(S) : Gourse et al.

It is certified that error appears in the above-identified patent and that said Letters Patent is hereby corrected as shown below:

Column 24,
Lines 4-5, delete "purified a and" and insert -- purified α and --

Column 25,
Line 64, delete "8385-8384" and insert -- 8385-8389 --

Column 26,
Line 42, delete "of the a subunit." and insert -- of the α subunit. --
Line 43, delete "C., applied to" and insert -- C, applied to --
Line 45, delete "C. for 90" and insert -- C for 90 --
Line 47, delete "concentration of a subunit" and insert -- concentration of α subunit --
Line 49, delete "of the a subunit" and insert -- of the α subunit --

Signed and Sealed this

Second Day of March, 2004

JON W. DUDAS
*Acting Director of the United States Patent and Trademark Office*